(12) United States Patent
Scholler et al.

(10) Patent No.: US 7,745,159 B2
(45) Date of Patent: *Jun. 29, 2010

(54) METHODS AND COMPOSITIONS FOR DIAGNOSING CARCINOMAS

(76) Inventors: Nathalie B Scholler, 6208 32nd Ave. Northwest, Seattle, WA (US) 98107; Ingegerd Hellstrom, 3925 NE. Surber Dr., Seattle, WA (US) 98105; Karl Erik Hellstrom, 3925 NE. Surber Dr., Seattle, WA (US) 98105

( * ) Notice: Subject to any disclaimer, the term of this patent is extended or adjusted under 35 U.S.C. 154(b) by 1343 days.

This patent is subject to a terminal disclaimer.

(21) Appl. No.: 10/778,617

(22) Filed: Feb. 13, 2004

(65) Prior Publication Data

US 2004/0142396 A1    Jul. 22, 2004

Related U.S. Application Data

(63) Continuation of application No. 09/513,597, filed on Feb. 25, 2000, now Pat. No. 6,770,445.

(60) Provisional application No. 60/147,494, filed on Aug. 5, 1999, provisional application No. 60/121,767, filed on Feb. 26, 1999.

(51) Int. Cl.
*A61K 39/395* (2006.01)

(52) U.S. Cl. .................. 435/7.8; 436/63; 436/64

(58) Field of Classification Search .................. None
See application file for complete search history.

(56) References Cited

U.S. PATENT DOCUMENTS

| | | | |
|---|---|---|---|
| 4,579,827 A | 4/1986 | Sakamoto et al. | 436/536 |
| 4,612,282 A | 9/1986 | Schlom et al. | 435/68 |
| 4,713,352 A | 12/1987 | Bander et al. | 436/548 |
| 4,737,579 A | 4/1988 | Hellström et al. | 530/387 |
| 4,753,894 A | 6/1988 | Frankel et al. | 436/548 |
| 4,906,562 A | 3/1990 | Hellstrom et al. | |
| 5,091,177 A | 2/1992 | Hellström et al. | |
| 5,525,337 A | 6/1996 | Willingham et al. | 424/156.1 |
| 5,633,142 A | 5/1997 | Herlyn et al. | 435/7.23 |
| 6,083,502 A | 7/2000 | Pastan et al. | 424/178.1 |

FOREIGN PATENT DOCUMENTS

WO    WO 97/25068    7/1997

OTHER PUBLICATIONS

Freshney, The Culture of Animal Cells, 1994, p. 5.*
Abstract of Bones et al (Tumour Biology, 2003, vol. 23, suppl., p. 41).*
Clark (Protein Engineering of Antibody Molecules for Prophylactic and Therapeutic Applications in Man, 1993, pp. 4-5).*
Andrew and Titus, ("Antibody Detection and preparation", In: Current protocols in Immunology, Margulies et al, Ed.s, 1991, pp. 2.7.1-2.7.7).*
Kerr and Thorpe (Immunochemistry LabFax, 1994, p. 175-177.*
Kerr and Thorpe (Immunochemistry LabFax, 1994, pp. vii-xi).*
Gebauer et al., 1998, Eur. J. Gynaecol. Oncol. 19(4):363-367 (Abstract Only).
Ho-Dac-Pannekeet et al., 1997, Kidney Int. 51(3):888-893 (Abstract Only).
Ho-Dac-Pannekeet et al., 1997, Adv. Peri. Dial. 13:17-22 (Abstract Only).
Kubonishi et al., 1997, Br. J. Haematol 98(2):450-452 (Abstract Only).
Luo et al., 1998, J. Biotechnol. 65(2-3):225-228 (Abstract Only).
Schlebusch et al., 1997, Hybridoma 16(1):47-52 (Abstract Only).
Allum et al., "Monoclonal Antibodies in the Diagnosis and Treatment of Malignant Conditions," *Surgery Annual 18*:41-64, 1986.
Bast et al., "A Radioimmunoassay Using a Monoclonal Antibody to Monitor the Course of Epithelial Ovarian Cancer," *New England J. of Medicine 309*(14):883-887, 1983.
Bell et al., "The Performance of Screening Tests for Ovarian Cancer: Results of a Systematic Review," *British J. of Obstetrics and Gynaecology 105*(11):1136-1147, 1998.
Blumenthal, R. et al., "Physiological Factors Influencing Radioantibody Uptake: a Study of Four Human Colonic Carcinomas," *Int J Cancer 51*(6):935-41, Jul. 1992.
Chang and Pastan, "Molecular Cloning and Expression of a cDNA Encoding a Protein Detected by the K1 Antibody from an Ovarian Carcinoma (Ovcar-3) Cell Line," *Int. J. Cancer 57*:90-97, 1994.
Chang and Pastan, "Molecular Cloning of Mesothelin, a Differentiation Antigen Present on Mesothelium, Mesotheliomas, and Ovarian Cancers," *Proc. Natl. Acad. Sci. USA 93*:136-140, 1996.
Chang et al., "Characterization of the Antigen (CAK1) Recognized by Monoclonal Antibody K1 Present on Ovarian Cancers and Normal Mesothelium," *Cancer Research 52*(1):181-186, 1992.
Chang et al., "Frequent Expression of the Tumor Antigen CAK1 in Squamous-Cell Carcinomas," *Int. J. Cancer 51*(4):548-554, 1992.
Chang et al., "Isolation and Characterization of a Monoclonal Antibody, K1, Reactive With Ovarian Cancers and Normal Mesothelium," *Int. J Cancer 50*(3):373-381, 1992.
Chang, K. et al., "Monoclonal Antibody K1 Reacts with Epithelial Mesothelioma but not with Lung Adenocarcinoma," *Am J Surg Pathol.* 16(3):259-68, Mar. 1992.
Chowdhury et al., "Isolation of a High-Affinity Stable Single-Chain Fv Specific for Mesothelin From DNA-Immunized Mice by Phage Display and Construction of a Recombinant Immunotoxin With Anti-Tumor Activity," *Proc. Natl. Acad. Sci. USA 95*(2):669-674, 1998.

(Continued)

*Primary Examiner*—Karen A Canella

(57) ABSTRACT

The invention is directed to compositions and methods for the detection of a malignant condition, and relates to the discovery of soluble forms of mesothelin polypeptides, including mesothelin related antigen (MRA). In particular the invention provides a nucleic acid sequence encoding MRA and an MRA variant. The invention also provides a method of screening for the presence of a malignant condition in a subject by detecting reactivity of an antibody specific for a mesothelin polypeptide with a molecule naturally occurring in soluble form in a sample from such a subject, and by hybridization screening using an MRA nucleotide sequence, as well as other related advantages.

27 Claims, 13 Drawing Sheets

OTHER PUBLICATIONS

Cioffi et al., "OVCA (CA 125) Second Generation: Technical Aspects and Serum Levels in Controls, Patients With Liver Disease, Pregnant Women and Patients With Ovarian Disease," *Tumori* 83(2):594-598, 1997.

Emery and Harris, "Strategies for Humaniing Antibodies," in Antibody Engineering, 2$^{nd}$ Ed., C. Borrebaeck, ed., 1995, pp. 159-160.

Fink and Clarke, "Monoclonal Antibodies as Diagnostic Reagents for the Identification and Characterization of Human Tumor Antigens," in *Progress in Clinical Pathology*, Grune & Stratton, Inc., New York, 1984, Chap. 6, vol. IX, pp. 121-133.

Gebauer and Müller-Ruchholtz, "Tumor Marker Concentrations in Normal and Malignant Tissues of Colorectal Cancer Patients and their Prognostic Relevance," *Anticancer Research* 17(4B):2939-2942, 1997.

Hellström et al., "Highly Tumor-Reactive, Internalizing, Mouse Monoclonal Antibodies to Le$^y$-Related Cell Surface Antigens," *Cancer Research* 50(7):2183-2190, 1990.

Hellström et al., "Monoclonal Antibodies Raised Against Human Lung Carcinoma," *Cancer Research* 46(8):3917-3923, 1986.

Hirokawa et al., "Neuroblastoma in an Adult with a High Serum Level of Carbohydrate Antigen, CA125: Report of a Case," *Surgery Today* 28:349-354, 1998.

Hollenbaugh et al., "Cleavable CD40Ig Fusion Proteins and the Binding to sgp39," *J. of Immunological Methods* 188:1-7, 1995.

Ind et al., "Serum Concentrations of Cancer Antigen 125, Placental Alkaline Phosphatase, Cancer-Associated Serum Antigen and Free Beta Human Chorionic Gonadotrophin as Prognostic Markers for Epithelial Ovarian Cancer," *British J. of Obstetrics and Gynaecology* 104(9):1024-1029, 1997.

Jäger et al., "Humoral Immune Responses of Cancer Patients against 'Cancer-Testis' Antigent NY-ESO-1: Correlation with Clinical Events," *Int. J. Cancer (Pred. Oncol.)*84:506-510, 1999.

Johnston, "Applications of Monoclonal Antibodies in Clinical Cytology as Exemplified by Studies With Monoclonal Antibody B72.3," *J. of Clinical Cytology and Cytopathology* 31(5):537-556, 1987.

Kabawat, S. et al., "Tissue Distribution of a Coelomic-Epithelium-Related Antigen Recognized by the Monoclonal Antibody OC125," *Int J Gynecol Pathol*. 2(3):275-85, 1983.

Kaplan et al., Clinical Chemistry (textbook), p. 44, 1984.

Kerr and Thorpe, "Purified antibodies" and "Biotinylation of Proteins," *Immunochemistry LabFax*, p. 20 and pp. 164-165, 1994.

Kerr and Thorpe, *Immunochemistry LabFax*, pp. 175-177 and 202-203, 1994.

Klein, J., "Self-nonself Discrimination, Histoincompatibility, and the Concept of Immunology," *Immunogenetics* 50(3-4):116-23, Nov. 1999.

Kohno et al. "Compositional Bias and Mimicry Toward the Nonself Proteome in Immunodominant T Cell Epitopes of Self and Nonself Antigens," *FASEB* 14, pp. 431-438, 2000.

Kojima et al., "Molecular Cloning and Expression of Megakaryocyte Potentiating Factor cDNA," *J. of Biological Chemistry* 270(37):21984-21990, 1995.

Kudoh et al., "Preoperative Determination of Several Serum Tumor Markers in Patients With Primary Epithelial Ovarian Carcinoma," *Gynecol. Obstet. Invest*. 47(1):52-57, 1999.

Kuroki et al., "Reducing Interference from Heterophilic Antibodies in a Two-site Immunoassay for Carcinoembryonic Antigen (CEA) by using a Human/Mouse Chimeric Antibody to CEA as the Tracer," *J. Immunological Methods* 180:81-91, 1995.

Lake et al., "Natural and Induced Human Antibody Response to Cancer," *Cancer Investigation* 18(5):480-489, 2000.

Lloyd et al., "Isolation and Characterization of Ovarian Cancer Antigen CA 125 Using a New Monoclonal Antibody (VK-8): Identification As a Mucin-type Molecule," *Int. J. Cancer* 71(5):842-850, 1997.

Meier et al., "CA125 Based Diagnosis and Therapy in Recurrent Ovarian Cancer," *Anticancer Research* 17(4B):3019-3020, 1997.

Meier et al., "Prognostic Significance of CA125 in Patients with Ovarian Cancer and Secondary Dubulking Surgery," *Anticancer Research* 17(4B):2945-2948, 1997.

Meier et al., "Significance of Tumor Marker Determinations in the Primary Therapy of Ovarian Cancer," *Anticancer Research* 17(4B):2949-2952, 1997.

Mensdorff-Pouilly et al., "Survival in Early Breast Cancer Patients is Favorably Influenced by a Natural Humoral Immune Response to Polymorphic Epithelial Mucin," *J. Clinical Oncology* 18(3):574-583, Feb. 2000.

Moore and Soper, "Clinical Utility of CA125 Levels in Predicting Laparoscopically Confirmed Salpingitis in Patients with Clinically Pelvic Inflammatory Disease," *Infect. Dis. Obstet. Gynecol.* 6:182-185, 1998.

Paul, W.E., Fundamental Immunology, 3$^{rd}$ ed., pp. 249-251, 1993.

Papsidero, "Recent Progress in the Immunological Monitoring of Carcinomas Using Monoclonal Antibodies," *Seminars in Surgical Oncology* 1(4):171-181, 1985.

Ristori, G. et al., "Compositional Bias and Mimicry Toward the Nonself Proteome in Immunodominant T Cell Epitopes of Self and Nonself Antigens," *FASEB J.* 14(3):431-8, Mar. 2000.

Sarandakou et al., "Tumour-Associated Antigens CEA, CA125, SCC and TPS in Gynaecological Cancer," *European J. Gynaecological Oncology XIX*(1):73-77, 1998.

Sarandakou et al., "Vaginal Fluid and Serum CEA, CA125 and SCC in Normal Conditions and in Benign and Malignant Diseases of the Genital Tract," *Acta Oncologica* 36:755-759, 1997.

Scholler et al., "Soluble Member(s) of the Mesothelin/Megakaryocyte Potentiating Factor Family Are Detectable in Sera From Patients with Ovarian Carcinoma," *Proc. Natl. Acad. Sci. USA* 96:11531-11536, 1999.

Schuurman et al., "Production of a Mouse/Human Chimeric IgE Monoclonal Antibody to the House Dust Mite Allergen Der p 2 and its use for the Absolute Quantification of Allergen-Specific IgE," *J. Allergy Clin. Immunol.* 99(4):545-550, Apr. 1997.

Shin et al., "Genetically-Engineered Antibodies: Tools for the Study of Diverse Properties of the Antibody Molecule," *Immunological Reviews* 130:87-107, 1992.

Welt, S. et al., "Antibodies in the Therapy of Colon Cancer," *Semin Oncol.* 26(6):683-90, Dec. 1999.

Yamaguchi et al., "A Novel Cytokine Exhibiting Megakaryocyte Potentiating Activity From a Human Pancreatic Tumor Cell Line HPC-Y5," *J. of Biological Chemistry* 269(2):805-808, 1994.

Yuan et al., "Establishment and Characterization of Human Ovarian Carcinoma Cell Lines," *Gynecologic Oncology* 66(3) :378-387, 1997.

\* cited by examiner

```
gaa gtg gag aag aca gcc tgt cct tca ggc aag aag gcc        48
Glu Val Glu Lys Thr Ala Cys Pro Ser Gly Lys Lys Ala
 1               5                  10                 15
cgc gag ata gac gag agc ctc atc ttc tac aag aag tgg gag ctg gaa   96
Arg Glu Ile Asp Glu Ser Leu Ile Phe Tyr Lys Lys Trp Glu Leu Glu
            20                  25                  30
gcc tgc gtg gat gcg gcc ctg ctg gcc acc cag atg gac cgc gtg aac  144
Ala Cys Val Asp Ala Ala Leu Leu Ala Thr Gln Met Asp Arg Val Asn
         35                  40                  45
gcc atc ccc ttc acc tac gag cag ctg gac gtc cta aag cat aaa ctg  192
Ala Ile Pro Phe Thr Tyr Glu Gln Leu Asp Val Leu Lys His Lys Leu
     50                  55                  60
gat gag ctc tac cca caa ggt tac ccc gag tct gtg atc cag cac ctg  240
Asp Glu Leu Tyr Pro Gln Gly Tyr Pro Glu Ser Val Ile Gln His Leu
 65                  70                  75                  80
ggc tac ctc ttc ctc aag atg agc cct gag gac att cgc aag tgg aat  288
Gly Tyr Leu Phe Leu Lys Met Ser Pro Glu Asp Ile Arg Lys Trp Asn
                 85                  90                  95
gtg acg tcc ctg gag acc ctg aag gct ttg ctt gaa gtc aac aaa ggg  336
Val Thr Ser Leu Glu Thr Leu Lys Ala Leu Leu Glu Val Asn Lys Gly
            100                 105                 110
cac gaa atg agt cct cag gtg gcc acc ctg atc gac cgc ttt gtg aag  384
His Glu Met Ser Pro Gln Val Ala Thr Leu Ile Asp Arg Phe Val Lys
        115                 120                 125
gga agg ggc cag cta gac aaa gac acc cta gac acc ctg acc gcc ttc  432
Gly Arg Gly Gln Leu Asp Lys Asp Thr Leu Asp Thr Leu Thr Ala Phe
    130                 135                 140
tac cct ggg tac ctg tgc tcc ctc agc ccc gag gag ctg agc tcc gtg  480
Tyr Pro Gly Tyr Leu Cys Ser Leu Ser Pro Glu Glu Leu Ser Ser Val
145                 150                 155                 160
ccc ccc agc agc atc tgg gcg gtc agg ccc cag gac ctg gac acg tgt  528
Pro Pro Ser Ser Ile Trp Ala Val Arg Pro Gln Asp Leu Asp Thr Cys
                165                 170                 175
gac cca agg cag ctg gac gtc ctc tat ccc aag gcc cgc ctt gct ttc  576
Asp Pro Arg Gln Leu Asp Val Leu Tyr Pro Lys Ala Arg Leu Ala Phe
            180                 185                 190
```

*Fig. 5A*

```
cag aac atg aac ggg tcc gaa tac ttc gtg aag atc cag tcc ttc ctg      624
Gln Asn Met Asn Gly Ser Glu Tyr Phe Val Lys Ile Gln Ser Phe Leu
            195                 200                 205
ggt ggg gcc ccc acg gag gat ttg aag gcg ctc agt cag cag aat gtg      672
Gly Gly Ala Pro Thr Glu Asp Leu Lys Ala Leu Ser Gln Gln Asn Val
    210                 215                 220
agc atg gac ttg gcc acg ttc atg aag ctg cgg acg gat gcg gtg ctg      720
Ser Met Asp Leu Ala Thr Phe Met Lys Leu Arg Thr Asp Ala Val Leu
225                 230                 235                 240
ccg ttg act gtg gct gag gtg cag aaa ctt ctg gga ccc cac gtg gag      768
Pro Leu Thr Val Ala Glu Val Gln Lys Leu Leu Gly Pro His Val Glu
                245                 250                 255
ggc ctg aag gcg gag gag cgg cac cgc ccg gtg cgg gac tgg atc cta      816
Gly Leu Lys Ala Glu Glu Arg His Arg Pro Val Arg Asp Trp Ile Leu
            260                 265                 270
cgg cag cgg cag gac gac ctg gac acg ctg ggg ctg ggg cta cag ggc      864
Arg Gln Arg Gln Asp Asp Leu Asp Thr Leu Gly Leu Gly Leu Gln Gly
    275                 280                 285
ggc atc ccc aac ggc tac ctg gtc cta gac ctc agc gtg caa ggt ggg      912
Gly Ile Pro Asn Gly Tyr Leu Val Leu Asp Leu Ser Val Gln Gly Gly
290                 295                 300
cgg ggc ggc cag gcc agg gct ggg ggc aga gct ggg ggc gtg gag gtg      960
Arg Gly Gly Gln Ala Arg Ala Gly Gly Arg Ala Gly Gly Val Glu Val
305                 310                 315                 320
ggc gct ctg agt cac ccc tct ctc tgt aga ggc cct ctc ggg gac gcc     1008
Gly Ala Leu Ser His Pro Ser Leu Cys Arg Gly Pro Leu Gly Asp Ala
                325                 330                 335
ctg cct cct agg acc tgg acc tgt tct cac cgt cct ggc act gct cct     1056
Leu Pro Pro Arg Thr Trp Thr Cys Ser His Arg Pro Gly Thr Ala Pro
            340                 345                 350
agc ctc cac cct ggc ctg agg gcc cca ctc cct tgc tgg ccc cag ccc     1104
Ser Leu His Pro Gly Leu Arg Ala Pro Leu Pro Cys Trp Pro Gln Pro
    355                 360                 365
tgc tgg gga tcc ccg cct ggc cag gag cag gca cgg gtg atc ccc gtt     1152
Cys Trp Gly Ser Pro Pro Gly Gln Glu Gln Ala Arg Val Ile Pro Val
370                 375                 380
cca ccc caa gag aac tcg cgc tca gta aac ggg aac atg ccc cct gca     1200
Pro Pro Gln Glu Asn Ser Arg Ser Val Asn Gly Asn Met Pro Pro Ala
385                 390                 395                 400
gac acg t                                                           1207
Asp Thr
```

*Fig. 5B*

```
EVEKTACPSG KKAREIDESL IFYKKWELEA CVDAALLATQ MDRVNAIPFT YEQLDVLKHK LDELYPQGYP ESVIQHLGYL FLKMSPEDIR
KWNVTSLETL KALLEVNKGH EMSPQVATLI DRFVKGRGQL DKDTLDTLTA FYPGYLCSLS PEELSSVPPS SIWAVRPQDL DTCDPRQLDV
LYPKARLAFQ NMNGSEYFVK IQSFLGGAPT EDLKALSQQN VSMDLATFMK LRTDAVLPLT VAEVQKLLGP HVEGLKAEER HRPVRDWILR
QRQDDLDTLG LGLQGGIPNG YLVLDLSVQG GRGGQARAGG RAGGVEVGAL SHPSLCRGPL GDALPPRTWT CSHRPGTAPS LHPGLRAPLP
CWPQPCWGSP PGQEQARVIP VPPQENSRSV NGNMPPADT
```

*Fig. 5C*

```
ttc cgg cgg gaa gtg gag aag aca gcc tgt cct tca ggc aag aag gcc     48
Phe Arg Arg Glu Val Glu Lys Thr Ala Cys Pro Ser Gly Lys Lys Ala
 1               5                  10                  15
cgc gag ata gac gag agc ctc atc ttc tac aag aag tgg gag ctg gaa     96
Arg Glu Ile Asp Glu Ser Leu Ile Phe Tyr Lys Lys Trp Glu Leu Glu
                20                  25                  30
gcc tgc gtg gat gcg gcc ctg ctg gcc acc cag atg gac cgc gtg aac    144
Ala Cys Val Asp Ala Ala Leu Leu Ala Thr Gln Met Asp Arg Val Asn
        35                  40                  45
gcc atc ccc ttc acc tac gag cag ctg gac gtc cta aag cat aaa ctg    192
Ala Ile Pro Phe Thr Tyr Glu Gln Leu Asp Val Leu Lys His Lys Leu
        50                  55                  60
gat gag ctc tac cca caa ggt tac ccc gag tct gtg atc cag cac ctg    240
Asp Glu Leu Tyr Pro Gln Gly Tyr Pro Glu Ser Val Ile Gln His Leu
 65                  70                  75                  80
ggc tac ctc ttc ctc aag atg agc cct gag gac att cgc aag tgg aat    288
Gly Tyr Leu Phe Leu Lys Met Ser Pro Glu Asp Ile Arg Lys Trp Asn
                85                  90                  95
gtg acg tcc ctg gag acc ctg aag gct ttg ctt gaa gtc aac aaa ggg    336
Val Thr Ser Leu Glu Thr Leu Lys Ala Leu Leu Glu Val Asn Lys Gly
                100                 105                 110
cac gaa atg agt cct cag gtg gcc acc ctg atc gac cgc ttt gtg aag    384
His Glu Met Ser Pro Gln Val Ala Thr Leu Ile Asp Arg Phe Val Lys
        115                 120                 125
gga agg ggc cag cta gac aaa gac acc cta gac acc ctg acc gcc ttc    432
Gly Arg Gly Gln Leu Asp Lys Asp Thr Leu Asp Thr Leu Thr Ala Phe
130                 135                 140
tac cct ggg tac ctg tgc tcc ctc agc ccc gag gag ctg agc tcc gtg    480
Tyr Pro Gly Tyr Leu Cys Ser Leu Ser Pro Glu Glu Leu Ser Ser Val
145                 150                 155                 160
ccc ccc agc agc atc tgg gcg gtc agg ccc cag gac ctg gac acg tgt    528
Pro Pro Ser Ser Ile Trp Ala Val Arg Pro Gln Asp Leu Asp Thr Cys
                165                 170                 175
gac cca agg cag ctg gac gtc ctc tat ccc aag gcc cgc ctt gct ttc    576
Asp Pro Arg Gln Leu Asp Val Leu Tyr Pro Lys Ala Arg Leu Ala Phe
                180                 185                 190
```

*Fig. 6A*

```
cag aac atg aac ggg tcc gaa tac ttc gtg aag atc cag tcc ttc ctg      624
Gln Asn Met Asn Gly Ser Glu Tyr Phe Val Lys Ile Gln Ser Phe Leu
            195                 200                 205
ggt ggg gcc ccc acg gag gat ttg aag gcg ctc agt cag cag aat gtg      672
Gly Gly Ala Pro Thr Glu Asp Leu Lys Ala Leu Ser Gln Gln Asn Val
        210                 215                 220
agc atg gac ttg gcc acg ttc atg aag ctg cgg acg gat gcg gtg ctg      720
Ser Met Asp Leu Ala Thr Phe Met Lys Leu Arg Thr Asp Ala Val Leu
225                 230                 235                 240
ccg ttg act gtg gct gag gtg cag aaa ctt ctg gga ccc cac gtg gag      768
Pro Leu Thr Val Ala Glu Val Gln Lys Leu Leu Gly Pro His Val Glu
                245                 250                 255
ggc ctg aag gcg gag gag cgg cac cgc ccg gtg cgg gac tgg atc cta      816
Gly Leu Lys Ala Glu Glu Arg His Arg Pro Val Arg Asp Trp Ile Leu
            260                 265                 270
cgg cag cgg cag gac gac ctg gac acg ctg ggg ctg ggg cta cag ggc      864
Arg Gln Arg Gln Asp Asp Leu Asp Thr Leu Gly Leu Gly Leu Gln Gly
        275                 280                 285
ggc atc ccc aac ggc tac ctg gtc cta gac ctc agc gtg caa ggt ggg      912
Gly Ile Pro Asn Gly Tyr Leu Val Leu Asp Leu Ser Val Gln Gly Gly
290                 295                 300
cgg ggc ggc cag gcc agg gct ggg ggc aga gct ggg ggc gtg gag gtg      960
Arg Gly Gly Gln Ala Arg Ala Gly Gly Arg Ala Gly Gly Val Glu Val
305                 310                 315                 320
ggc gct ctg agt cac ccc tct ctc t
Gly Ala Leu Ser His Pro Ser Leu
```

*Fig. 6B*

```
FRREVEKTAC PSGKKAREID ESLIFYKKWE LEACVDAALL ATQMDRVNAI PFTYEQLDVL KHKLDELYPQ GYPESVIQHL GYLFLKMSPE
DIRKWNVTSL ETLKALLEVN KGHEMSPQVA TLIDRFVKGR GQLDKDTLDT LTAFYPGYLC SLSPEELSSV PPSSIWAVRP QDLDTCDPRQ
LDVLYPKARL AFQNMNGSEY FVKIQSFLGG APTEDLKALS QQNVSMDLAT FMKLRTDAVL PLTVAEVQKL LGPHVEGLKA EERHRPVRDW
ILRQRQDDLD TLGLGLQGGI PNGYLVLDLS VQGGRGGQAR AGGRAGGVEV GALSHPSL
```

*Fig. 6C*

```
ttc cgg cgg gaa gtg gag aag aca gcc tgt cct tca ggc aag aag gcc      48
Phe Arg Arg Glu Val Glu Lys Thr Ala Cys Pro Ser Gly Lys Lys Ala
 1               5                  10                  15
cgc gag ata gac gag agc ctc atc ttc tac aag aag tgg gag ctg gaa      96
Arg Glu Ile Asp Glu Ser Leu Ile Phe Tyr Lys Lys Trp Glu Leu Glu
                20                  25                  30
gcc tgc gtg gat gcg gcc ctg ctg gcc acc cag atg gac cgc gtg aac     144
Ala Cys Val Asp Ala Ala Leu Leu Ala Thr Gln Met Asp Arg Val Asn
            35                  40                  45
gcc atc ccc ttc acc tac gag cag ctg gac gtc cta aag cat aaa ctg     192
Ala Ile Pro Phe Thr Tyr Glu Gln Leu Asp Val Leu Lys His Lys Leu
        50                  55                  60
gat gag ctc tac cca caa ggt tac ccc gag tct gtg atc cag cac ctg     240
Asp Glu Leu Tyr Pro Gln Gly Tyr Pro Glu Ser Val Ile Gln His Leu
 65                 70                  75                  80
ggc tac ctc ttc ctc aag atg agc cct gag gac att cgc aag tgg aat     288
Gly Tyr Leu Phe Leu Lys Met Ser Pro Glu Asp Ile Arg Lys Trp Asn
                85                  90                  95
gtg acg tcc ctg gag acc ctg aag gct ttg ctt gaa gtc aac aaa ggg     336
Val Thr Ser Leu Glu Thr Leu Lys Ala Leu Leu Glu Val Asn Lys Gly
                100                 105                 110
cac gaa atg agt cct cag gtg gcc acc ctg atc gac cgc ttt gtg aag     384
His Glu Met Ser Pro Gln Val Ala Thr Leu Ile Asp Arg Phe Val Lys
        115                 120                 125
gga agg ggc cag cta gac aaa gac acc cta gac acc ctg acc gcc ttc     432
Gly Arg Gly Gln Leu Asp Lys Asp Thr Leu Asp Thr Leu Thr Ala Phe
        130                 135                 140
tac cct ggg tac ctg tgc tcc ctc agc ccc gag gag ctg agc tcc gtg     480
Tyr Pro Gly Tyr Leu Cys Ser Leu Ser Pro Glu Glu Leu Ser Ser Val
145                 150                 155                 160
ccc ccc agc agc atc tgg gcg gtc agg ccc cag gac ctg gac acg tgt     528
Pro Pro Ser Ser Ile Trp Ala Val Arg Pro Gln Asp Leu Asp Thr Cys
                165                 170                 175
gac cca agg cag ctg gac gtc ctc tat ccc aag gcc cgc ctt gct ttc     576
Asp Pro Arg Gln Leu Asp Val Leu Tyr Pro Lys Ala Arg Leu Ala Phe
            180                 185                 190
cag aac atg aac ggg tcc gaa tac ttc gtg aag atc cag tcc ttc ctg     624
Gln Asn Met Asn Gly Ser Glu Tyr Phe Val Lys Ile Gln Ser Phe Leu
        195                 200                 205
```

*Fig. 7A*

```
ggt ggg gcc ccc acg gag gat ttg aag gcg ctc agt cag cag aat gtg        672
Gly Gly Ala Pro Thr Glu Asp Leu Lys Ala Leu Ser Gln Gln Asn Val
210                 215                 220
agc atg gac ttg gcc acg ttc atg aag ctg cgg acg gat gcg gtg ctg        720
Ser Met Asp Leu Ala Thr Phe Met Lys Leu Arg Thr Asp Ala Val Leu
225                 230                 235                 240
ccg ttg act gtg gct gag gtg cag aaa ctt ctg gga ccc cac gtg gag        768
Pro Leu Thr Val Ala Glu Val Gln Lys Leu Leu Gly Pro His Val Glu
                    245                 250                 255
ggc ctg aag gcg gag gag cgg cac cgc ccg gtg cgg gac tgg atc cta        816
Gly Leu Lys Ala Glu Glu Arg His Arg Pro Val Arg Asp Trp Ile Leu
        260                 265                 270
cgg cag cgg cag gac gac ctg gac acg ctg ggg ctg ggg cta cag ggc        864
Arg Gln Arg Gln Asp Asp Leu Asp Thr Leu Gly Leu Gly Leu Gln Gly
            275                 280                 285
ggc atc ccc aac ggc tac ctg gtc cta gac ctc agc gtg caa ggt ggg        912
Gly Ile Pro Asn Gly Tyr Leu Val Leu Asp Leu Ser Val Gln Gly Gly
290                 295                 300
cgg ggc ggc cag gcc agg gct ggg ggc aga gct ggg ggc gtg gag gtg        960
Arg Gly Gly Gln Ala Arg Ala Gly Gly Arg Ala Gly Gly Val Glu Val
305                 310                 315                 320
ggc gct ctg agt cac ccc tct ctc tgt aga ggc cct ctc ggg gac gcc       1008
Gly Ala Leu Ser His Pro Ser Leu Cys Arg Gly Pro Leu Gly Asp Ala
                    325                 330                 335
ctg cct cct agg acc tgg acc tgt tct cac cgt cct ggc act gct cct       1056
Leu Pro Pro Arg Thr Trp Thr Cys Ser His Arg Pro Gly Thr Ala Pro
                340                 345                 350
agc ctc cac cct ggc ctg agg gcc cca ctc cct tgc tgg ccc cag ccc       1104
Ser Leu His Pro Gly Leu Arg Ala Pro Leu Pro Cys Trp Pro Gln Pro
        355                 360                 365
tgc tgg gga tcc ccg cct ggc cag gag cag gca cgg gtg atc ccc gtt       1152
Cys Trp Gly Ser Pro Pro Gly Gln Glu Gln Ala Arg Val Ile Pro Val
            370                 375                 380
cca ccc caa gag aac tcg cgc tca gta aac ggg aac atg ccc cct gca       1200
Pro Pro Gln Glu Asn Ser Arg Ser Val Asn Gly Asn Met Pro Pro Ala
385                 390                 395                 400
gac acg t                                                              1207
Asp Thr
```

*Fig. 7B*

```
FRREVEKTAC PSGKKAREID ESLIFYKKWE LEACVDAALL ATQMDRVNAI PFTYEQLDVL KHKLDELYPQ GYPESVIQHL GYLFLKMSPE
DIRKWNVTSL ETLKALLEVN KGHEMSPQVA TLIDRFVKGR GQLDKDTLDT LTAFYPGYLC SLSPEELSSV PPSSIWAVRP QDLDTCDPRQ
LDVLYPKARL AFQNMNGSEY FVKIQSFLGG APTEDLKALS QQNVSMDLAT FMKLRTDAVL PLTVAEVQKL LGPHVEGLKA EERHRPVRDW
ILRQRQDDLD TLGLGLQGGI PNGYLVLDLS VQGGRGGQAR AGGRAGGVEV GALSHPSLCR GPLGDALPPR TWTCSHRPGT APSLHPGLRA
PLPCWPQPCW GSPPGQEQAR VIPVPPQENS RSVNGNMPPA DT
```

*Fig. 7C*

METHODS AND COMPOSITIONS FOR DIAGNOSING CARCINOMAS

CROSS-REFERENCES TO RELATED APPLICATIONS

This application is a continuation of U.S. patent application Ser. No. 09/513,597, filed Feb. 25, 2000, which claims the benefit of U.S. Provisional Patent Application No. 60/147,494, filed Aug. 5, 1999, and U.S. Provisional Patent Application No. 60/121,767, filed Feb. 26, 1999, which applications are incorporated herein by reference in their entireties.

BACKGROUND OF THE INVENTION

Cancer includes a broad range of diseases, affecting approximately one in four individuals worldwide. The severity of the adverse impact of cancer cannot be understated, influencing medical policy and procedure as well as society generally. Because a hallmark of many types of cancer is rapid and unregulated proliferation of malignant cells, an overarching problem in improving approaches to cancer is the need for early detection and diagnosis. Numerous attempts have been made to develop accurate and reliable criteria for diagnosing the presence of a malignant condition. In particular, efforts have been directed to the use of serologically defined antigenic markers known as tumor associated antigens, which are either uniquely expressed by cancer cells or are present at markedly higher levels in subjects having a malignant condition.

However, due to the high heterogeneity of tumor associated antigen expression, for example the extreme diversity of carcinoma antigens, there is a need for additional tumor markers that are useful in cancer diagnosis. Many monoclonal antibodies reactive with carcinoma associated antigens are known (see, e.g., Papsidero, 1985 *Semin. Surg. Oncol.* 1:171, Allum et al., 1986 *Surg. Ann.* 18:41). These and other described monoclonal antibodies bind to a variety of different carcinoma associated antigens including glycoproteins, glycolipids and mucins (see, e.g., Fink et al., 1984 *Prog. Clin. Pathol.* 9:121; U.S. Pat. No. 4,737,579; U.S. Pat. No. 4,753,894; U.S. Pat. No. 4,579,827; U.S. Pat. No. 4,713,352). Many such monoclonal antibodies recognize tumor associated antigens that exhibit restricted expression on some but not other tumors originating in a given cell lineage or tissue type.

There are only relatively few examples of tumor associated antigens that appear to be useful for identifying a particular type of malignancy. Monoclonal antibody B72.3, for example, specifically binds to a high molecular mass ($>10^6$ Da) tumor-associated mucin antigen that is selectively expressed on a number of different carcinomas, including most if not all ovarian carcinomas and an overwhelming majority of non-small cell lung carcinomas, colon carcinomas and breast carcinomas (see, e.g., Johnston, 1987 *Acta Cytol.* 1:537; U.S. Pat. No. 4,612,282). Nevertheless, detection of cell-associated tumor markers such as the mucin antigen recognized by B72.3 following surgical resection of a tumor may be of limited usefulness for diagnostic screening, in which early detection of a malignant condition prior to accumulation of substantial tumor mass is preferred.

An alternative to the diagnosis of a particular type of cancer by screening surgically resected specimens for tumor associated antigens, where invasive surgery is usually indicated only after detection of an accumulated tumor mass, would be to provide compositions and methods for detecting such antigens in samples obtained from subjects by non-invasive or minimally invasive procedures. In ovarian and other carcinomas, for example, there are currently a number of soluble tumor associated antigens that are detectable in samples of readily obtained biological fluids such as serum or mucosal secretions. One such marker is CA125, a carcinoma associated antigen that is also shed into the bloodstream, where it is detectable in serum (e.g., Bast et al., 1983 *N. Eng. J. Med.* 309:883; Lloyd et al., 1997 *Int. J. Canc.* 71:842). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN) and placental alkaline phosphatase (PLAP), in efforts to provide diagnostic and/or prognostic profiles of ovarian and other carcinomas (e.g., Sarandakou et al., 1997 *Acta Oncol.* 36:755; Sarandakou et al., 1998 *Eur. J. Gynaecol. Oncol.* 19:73; Meier et al., 1997 *Anticanc. Res.* 17(4B):2945; Kudoh et al., 1999 *Gynecol. Obstet. Invest.* 47:52; Ind et al., 1997 *Br. J. Obstet. Gynaecol.* 104:1024; Bell et al. 1998 *Br. J. Obstet. Gynaecol.* 105:1136; Cioffi et al., 1997 *Tumori* 83:594; Meier et al. 1997 *Anticanc. Res.* 17(4B):2949; Meier et al., 1997 *Anticanc. Res.* 17(4B):3019).

Elevated levels of serum CA125 alone or in combination with other known indicators, however, do not provide a definitive diagnosis of malignancy, or of a particular malignancy such as ovarian carcinoma. For example, elevated CA125, CEA and SCC in vaginal fluid and serum correlate most strongly with inflammation in benign gynecological diseases, relative to cervical cancer and genital tract cancers (e.g., Moore et al., 1998 *Infect. Dis. Obstet. Gynecol.* 6:182; Sarandakou et al., 1997 *Acta Oncol.* 36:755). As another example, elevated serum CA125 may also accompany neuroblastoma (e.g., Hirokawa et al., 1998 *Surg. Today* 28:349), while elevated CEA and SCC, among others, may accompany colorectal cancer (Gebauer et al., 1997 *Anticanc. Res.* 17(4B):2939). Thus the compelling need for additional markers to be used, including markers useful in multi-factor diagnostic screening, is apparent. (See, e.g., Sarandakou et al., 1998; Kudoh et al., 1999; Ind et al., 1997.)

The differentiation antigen mesothelin is expressed on the surfaces of normal mesothelial cells and also on certain cancer cells, including epithelial ovarian tumors and mesotheliomas. Also known as CAK1, mesothelin is identified by its reactivity with the monoclonal antibody K-1 (MAb K-1), which was generated following immunization with the OVCAR-3 ovarian carcinoma cell line (Chang et al., 1992 *Canc. Res.* 52:181; Chang et al., 1992 *Int. J. Canc.* 50:373; Chang et al., 1992 *Int. J. Canc.* 51:548; Chang et al., 1996 *Proc. Nat. Acad. Sci. USA* 93:136; Chowdhury et al., 1998 *Proc. Nat. Acad. Sci. USA* 95:669). Mesothelin is synthesized as an approximately 70 kDa glycoprotein precursor having a C-terminal glycosylphosphatidylinositol (GPI) linkage site for cell membrane attachment. This precursor is processed by, inter alia, proteolytic cleavage into at least two components: (i) a shed N-terminal ~31 kDa polypeptide (Chowdhury et al., 1998 *Proc. Nat. Acad. Sci. USA* 95:669) having extraordinarily high homology to a soluble 31 kDa polypeptide known as megakaryocyte potentiating factor (MPF) that is similarly derived by proteolysis of an approximately 70 kDa GPI-linked glycoprotein precursor belonging to the mesothelin polypeptide family (Yamaguchi et al., 1994 *J. Biol. Chem.* 269:805; Kojima et al., 1995 *J. Biol. Chem.* 270:21984; and (ii) a mature 40 kDa GPI-linked, cell surface-bound C-terminal mesothelin glycosylated polypeptide, which bears the K-1 (MAb K-1) recognition epitope (Chang et al., 1996). As defined by reactivity with MAb K-1, mesothelin is present on a majority of squamous cell carcinomas including epithelial ovarian, cervical and esophageal tumors, and on mesotheliomas (Chang et al., 1992 *Canc. Res.* 52:181; Chang et al., 1992 *Int. J. Canc.* 50:373; Chang et al., 1992 *Int. J. Canc.* 51:548; Chang et al., 1996 *Proc. Nat. Acad. Sci. USA* 93:136; Chowdhury et al., 1998 Proc. Nat. Acad. Sci. USA 95:669). Using MAb K-1, mesothelin is detectable only as a cell-associated tumor marker and has not been found in serum from ovarian cancer patients, or in medium conditioned by OVCAR-3 cells (Chang et al., 1992 *Int. J. Cancer* 50:373). Thus mesothelin, despite an expression pattern that correlates with specific malignant conditions, does not appear to offer a useful marker for early diagnostic screening, because only cell-associated and not soluble forms of mesothelin may be detectable by known methods.

The compositions and methods of the present invention overcome these limitations of the prior art by providing a method of screening for the presence of a malignant condition using antibodies specific for mesothelin/MPF and/or mesothelin/MPF-related antigens to detect polypeptides that naturally occur in soluble form, and offer other related advantages.

SUMMARY OF THE INVENTION

The present invention is directed to compositions and methods useful in screening for the presence of a malignant condition in a subject. In particular, the invention relates to the unexpected finding that soluble mesothelin polypeptides, or molecules naturally occurring in soluble form and having an antigenic determinant reactive with at least one antibody that is specific for a mesothelin polypeptide, can be detected in a biological sample from a subject.

It is one aspect of the invention to provide a method of screening for the presence of a malignant condition in a subject comprising contacting a biological sample from a subject with at least one antibody specific for a mesothelin related antigen polypeptide to determine the presence in the biological sample of a molecule naturally occurring in soluble form in the sample and having an antigenic determinant that is reactive with the at least one antibody, under conditions and for a time sufficient to detect binding of the antibody to the antigenic determinant, and therefrom detecting the presence of a malignant condition. In some embodiments the biological sample is blood, serum, serosal fluid, plasma, lymph, urine, cerebrospinal fluid, saliva, a mucosal secretion, a vaginal secretion, ascites fluid, pleural fluid, pericardial fluid, peritoneal fluid, abdominal fluid, culture medium, conditioned culture medium or lavage fluid.

In certain other embodiments, the mesothelin related antigen polypeptide comprises a polypeptide having the amino acid sequence set forth in SEQ ID NO:1 or in SEQ ID NO:2 or a fragment or derivative thereof. In another embodiment the mesothelin related antigen polypeptide variant is a splice variant.

In certain embodiments of the invention, the antibody comprises a polyclonal antibody, and in other embodiments the antibody comprises an affinity purified antibody. In particularly preferred embodiments the antibody comprises a monoclonal antibody. In another embodiment the antibody comprises a recombinant antibody and in another embodiment the antibody comprises a chimeric antibody. In another embodiment, the antibody comprises a humanized antibody. In another embodiment, the antibody comprises a single chain antibody.

In some embodiments of the invention, detection of binding of the antibody to an antigenic determinant comprises detection of a radionuclide. In other embodiments, detection of binding of the antibody to an antigenic determinant comprises detection of a fluorophore. In another embodiment, detection of binding of the antibody to an antigenic determinant comprises detection of a binding event between an avidin molecule and a biotin molecule and in another embodiment detection of binding of the antibody to an antigenic determinant comprises detection of a binding event between a streptavidin molecule and a biotin molecule. In certain embodiments detection of binding of the antibody to an antigenic determinant comprises spectrophotometric detection of a product of an enzyme reaction. In some embodiments of the invention, the at least one antibody is detectably labeled, while in certain other embodiments the at least one antibody is not detectably labeled and detection of binding of the antibody to an antigenic determinant is indirect.

According to certain embodiments of the invention, the malignant condition may be adenocarcinoma, mesothelioma, ovarian carcinoma, pancreatic carcinoma or non-small cell lung carcinoma.

It is another aspect of the invention to provide a method of screening for the presence of a malignant condition in a subject comprising contacting a biological sample from a subject with at least one antibody to determine the presence in the biological sample of a molecule naturally occurring in soluble form in the sample and having an antigenic determinant that is reactive with the at least one antibody, the antigen combining site of which competitively inhibits the immunospecific binding of a monoclonal antibody that is OV569, MAb K-1, 4H3, 3G3 or 1A6, under conditions and for a time sufficient to detect binding of the antibody to the antigenic determinant, and therefrom detecting the presence of a malignant condition.

Another aspect of the invention provides a method of screening for the presence of a malignant condition in a subject comprising contacting a biological sample from a subject with at least one antibody to determine the presence in the biological sample of a molecule naturally occurring in soluble form in the sample and having an antigenic determinant that is reactive with the antibody, the antigen combining site of which competitively inhibits the immunospecific binding of monoclonal antibody OV569, under conditions and for a time sufficient to detect binding of the antibody to the antigenic determinant, and therefrom detecting the presence of a malignant condition.

Still another aspect of the invention provides a method of screening for the presence of a malignant condition in a subject comprising contacting a biological sample from a subject with at least one antibody specific for a human mesothelin related antigen polypeptide to determine the presence in the biological sample of a molecule naturally occurring in soluble form in the sample and having an antigenic determinant that is reactive with the antibody, under conditions and for a time sufficient to detect binding of the at least one antibody to the antigenic determinant, wherein the at least one antibody immunospecifically binds to mesothelin related antigen, and therefrom detecting the presence of a malignant condition. In certain embodiments, the mesothelin related antigen is also immunospecifically reactive with monoclonal antibody MAb K-1.

Turning to another aspect, the invention provides a method of screening for the presence of a malignant condition in a subject comprising contacting a biological sample from a subject with at least one antibody specific for a human mesothelin related antigen polypeptide to determine the presence in the biological sample of a molecule naturally occurring in soluble form in the sample and having an antigenic determinant that is reactive with the at least one antibody, the antigen combining site of which competitively inhibits the immunospecific binding of a monoclonal antibody that is OV569, MAb K-1, 4H3, 3G3 or 1A6, under conditions and for a time sufficient to detect binding of the antibody to the antigenic determinant, wherein the at least one antibody immunospecifically binds to mesothelin related antigen, and therefrom detecting the presence of a malignant condition. In certain embodiments the mesothelin related antigen is also immunospecifically reactive with monoclonal antibody MAb K-1.

Turning to another aspect, the invention provides a method of screening for the presence of a malignant condition in a subject comprising contacting a biological sample from a subject with at least one immobilized first antibody specific for a mesothelin related antigen polypeptide to determine the presence in the biological sample of a molecule naturally occurring in soluble form in the sample, under conditions and for a time sufficient to specifically bind the at least one immobilized first antibody to the mesothelin related antigen polypeptide and thereby form an immune complex; removing constituents of the sample that do not specifically bind to the at least one immobilized first antibody; and contacting the immune complex with at least one second antibody specific for a mesothelin related antigen polypeptide, wherein the antigen combining site of the at least one second antibody does not competitively inhibit the antigen combining site of the at least one immobilized first antibody, under conditions and for a time sufficient to detect specific binding of the at least one second antibody to the mesothelin related antigen polypeptide, and therefrom detecting the presence of a malignant condition.

In yet another aspect the invention provides a method of screening for the presence of a malignant condition in a subject comprising contacting a biological sample from a subject with at least one immobilized first antibody specific for a mesothelin related antigen polypeptide to determine the presence in the biological sample of a molecule naturally occurring in soluble form in the sample, wherein the antigen combining site of the at least one first antibody competitively inhibits the immunospecific binding of monoclonal antibody OV569 under conditions and for a time sufficient to specifically bind the at least one immobilized first antibody to the mesothelin related antigen polypeptide and thereby form an immune complex; removing constituents of the sample that do not specifically bind to the at least one immobilized first antibody; and contacting the immune complex with at least one second antibody specific for a mesothelin related antigen polypeptide, wherein the antigen combining site of the at least one second antibody does not competitively inhibit the immunospecific binding of monoclonal antibody OV569, under conditions and for a time sufficient to detect specific binding of the at least one second antibody to the mesothelin related antigen polypeptide, and therefrom detecting the presence of a malignant condition.

In another aspect, the invention provides a method of screening for the presence of a malignant condition in a subject comprising contacting a biological sample from a subject with at least one immobilized first antibody specific for a mesothelin related antigen polypeptide to determine the presence in the biological sample of a molecule naturally occurring in soluble form in the sample, wherein the antigen combining site of the at least one first antibody competitively inhibits the immunospecific binding of monoclonal antibody MAb K-1 under conditions and for a time sufficient to specifically bind the at least one immobilized first antibody to the mesothelin related antigen polypeptide and thereby form an immune complex; removing constituents of the sample that do not specifically bind to the at least one immobilized first antibody; and contacting the immune complex with at least one second antibody specific for a mesothelin related antigen polypeptide, wherein the antigen combining site of the at least one second antibody does not competitively inhibit the immunospecific binding of monoclonal antibody MAb K-1, under conditions and for a time sufficient to detect specific binding of the at least one second antibody to the mesothelin related antigen polypeptide, and therefrom detecting the presence of a malignant condition.

In certain embodiments the subject invention method further comprises determining the presence in the sample of at least one soluble marker of a malignant condition, wherein the marker is carcinoembryonic antigen, CA125, sialyl TN, squamous cell carcinoma antigen, tissue polypeptide antigen, or placental alkaline phosphatase.

It is another aspect of the invention to provide a method of screening for the presence of a malignant condition in a subject comprising contacting each of (i) a first biological sample from a first subject suspected of having a malignant condition, and (ii) a second biological sample from a second subject known to be free of a malignant condition, with at least one antibody specific for a mesothelin related antigen polypeptide to determine the presence in each of the first and second biological samples of a molecule naturally occurring in soluble form in the samples and having an antigenic determinant that is reactive with the at least one antibody, under conditions and for a time sufficient to detect binding of the antibody to the antigenic determinant, and comparing a level of detectable binding of the antibody to the antigenic determinant in the first biological sample to a level of detectable binding of the antibody to the antigenic determinant in the second biological sample, and therefrom detecting the presence of a malignant condition.

In another aspect, the invention provides a method of screening for the presence of a malignant condition in a subject comprising detecting in a biological sample from the subject the presence of an antibody that immunospecifically binds to a mesothelin related antigen polypeptide. In certain embodiments the mesothelin related antigen polypeptide comprises a polypeptide having the amino acid sequence of SEQ ID NO:1 or SEQ ID NO:2 or SEQ ID NO:13.

Turning to another aspect, the invention provides an antibody specific for a human mesothelin related antigen polypeptide, comprising a monoclonal immunoglobulin variable region that does not competitively inhibit the immunospecific binding of monoclonal antibody Mab K-1 to a mesothelin polypeptide and that specifically binds to a mesothelin related antigen polypeptide comprising the amino acid sequence set forth in SEQ ID NO:1 or in SEQ ID NO:2 or in SEQ ID NO:13. In certain embodiments the antibody is a fusion protein, while in certain other embodiments the antibody is a single chain antibody. In certain other embodiments, the mesothelin related antigen polypeptide further comprises a glycosylated mesothelin polypeptide. In another embodiment, the mesothelin related antigen polypeptide has an apparent molecular weight of approximately 42 to 45 kilodaltons. In certain embodiments the antibody is monoclonal antibody OV569, 4H3, 3G3 or 1A6.

In still another aspect, the invention provides a method of screening for the presence of a malignant condition in a subject comprising contacting a biological sample from a subject with a detectably labeled mesothelin related antigen polypeptide, under conditions and for a time sufficient to detect binding to the mesothelin related antigen polypeptide of an antibody naturally occurring in soluble form in the sample, and therefrom detecting the presence of a malignant condition.

Turning to another aspect, the invention provides an isolated nucleic acid molecule that is a nucleic acid molecule encoding a mesothelin related antigen polypeptide, the polypeptide comprising an amino acid sequence set forth in SEQ ID NO:1 or in SEQ ID NO:2 or in SEQ ID NO:13; or that is a nucleic acid molecule that encodes a mesothelin related antigen polypeptide and that is capable of hybridizing to such a nucleic acid molecule encoding a mesothelin related antigen under moderately stringent conditions, wherein the isolated nucleic acid molecule is not a nucleic acid molecule consisting of the nucleotide sequence set forth in SEQ ID NO:15, the nucleotide sequence set forth in SEQ ID NO:16, the nucleotide sequence set forth in SEQ ID NO:17 or the nucleotide sequence set forth in SEQ ID NO:18. In certain embodiments the invention provides an antisense oligonucleotide comprising at least 15 consecutive nucleotides complementary to the nucleic acid molecule encoding a mesothelin related antigen polypeptide.

In other embodiments, the present invention provides a fusion protein comprising a polypeptide sequence fused to a mesothelin related antigen polypeptide. In certain further embodiments, the polypeptide is an enzyme or a variant or fragment thereof. In certain further embodiments, the polypeptide sequence fused to a mesothelin related antigen polypeptide is cleavable by a protease. In another embodiment, the polypeptide sequence is an affinity tag polypeptide having affinity for a ligand.

In other embodiments, the invention provides a recombinant expression construct comprising at least one promoter operably linked to a nucleic acid molecule encoding a mesothelin related antigen polypeptide as described above. In certain embodiments the promoter is a regulated promoter and in certain other embodiments the mesothelin related antigen polypeptide is expressed as a fusion protein with a polypeptide product of a second nucleic acid sequence. In a further embodiment the polypeptide product of the second nucleic acid sequence is an enzyme. In another embodiment the expression construct is a recombinant viral expression construct. According to other embodiments, the invention provides a host cell comprising a recombinant expression construct as provided herein. In one embodiment the host cell is a prokaryotic cell and in another embodiment the host cell is a eukaryotic cell.

In another aspect, the invention provides a method of producing a recombinant mesothelin related antigen polypeptide by culturing a host cell comprising a recombinant expression construct comprising at least one promoter operably linked to a nucleic acid molecule encoding a mesothelin related antigen polypeptide as provided herein. In certain embodiments the promoter is a regulated promoter. In another embodiment the invention provides a method of producing a recombinant mesothelin related antigen polypeptide, by culturing a host cell infected with the recombinant viral expression construct as provided herein for expression of recombinant mesothelin related antigen polypeptide.

The present invention also provides, in another embodiment, a method for detecting mesothelin related antigen expression in a sample by contacting an antisense oligonucleotide as described above with a sample comprising a nucleic acid sequence encoding a mesothelin related antigen polypeptide having the amino acid sequence set forth in SEQ ID NO:13, or a fragment or variant thereof; and detecting in the sample an amount of mesothelin related antigen polypeptide-encoding nucleic acid that hybridizes to the antisense oligonucleotide, and therefrom detecting mesothelin related antigen expression in the sample. In another embodiment the amount of mesothelin related antigen polypeptide-encoding nucleic acid that hybridizes to the antisense oligonucleotide is determined using polymerase chain reaction. In another embodiment the amount of mesothelin related antigen polypeptide-encoding nucleic acid that hybridizes to the antisense oligonucleotide is determined using a hybridization assay. In another embodiment the sample comprises an RNA or cDNA preparation.

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE DRAWINGS

FIGS. 5A-B shows a mesothelin related antigen (MRA-1) amino acid sequence (SEQ ID NO:1) and a nucleic acid sequence (SEQ ID NO:3) encoding the MRA-1 mesothelin related antigen. Amino acid and nucleotide positions are numbered according to the MRA-2 sequence (FIGS. 6A-B) which begins with three additional N-terminal amino acids (nine additional 5' nucleotides). Highlighted in bold type is the 82 base insertion relative to the related mesothelin/MPF sequences. FIG. 5C shows amino acid sequence using single letter code.

FIGS. 6A-C shows a mesothelin related antigen (MRA-2) amino acid sequence (SEQ ID NO:2) and a nucleic acid sequence (SEQ ID NO:4) encoding the MRA-2 mesothelin related antigen, which begins with three additional N-terminal amino acids (nine additional 5' nucleotides). Highlighted in bold type are 80 nucleotides of the 82 base insertion relative to the related mesothelin/MPF sequences. FIGS. 6A-B shows amino acid sequence using single letter code.

FIGS. 7A-B shows a soluble mesothelin related (SMR) antigen amino acid sequence (SEQ ID NO:13) and a nucleic acid sequence (SEQ ID NO:14) encoding this SMR. Highlighted in bold type is the 82 base insertion relative to the related mesothelin/MPF sequences. FIG. 7C shows amino acid sequence using single letter code.

DETAILED DESCRIPTION OF THE INVENTION

Figure 1:
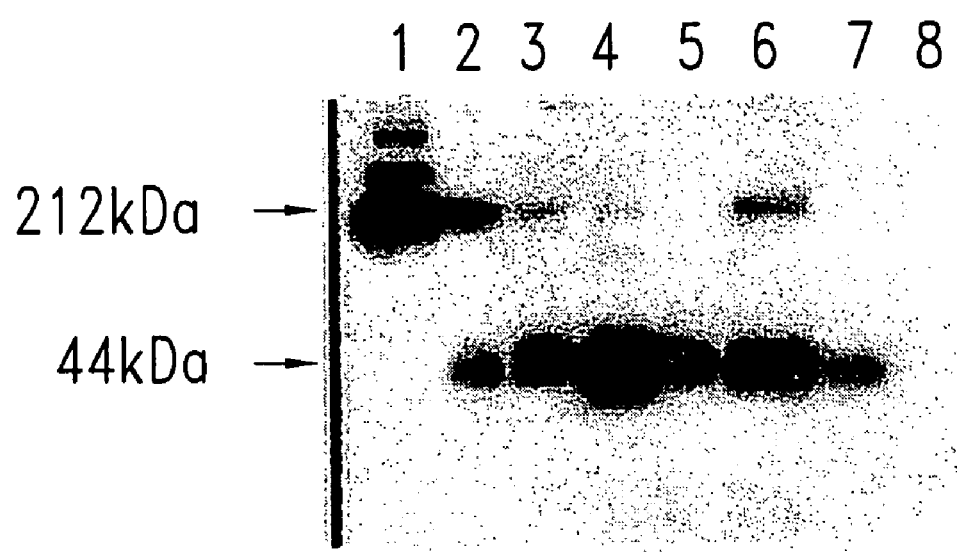
FIG. 1 shows Western immunoblot characterization of the carcinoma associated antigen detected by monoclonal antibody OV569.

The present invention pertains in part to the unexpected discovery that soluble forms of certain gene products referred to herein as mesothelin polypeptides occur naturally in subjects, including elevated levels of such soluble mesothelin polypeptides in subjects having certain carcinomas. The invention therefore provides useful compositions and methods for the detection and diagnosis of a malignant condition in a subject by specific detection of such soluble mesothelin polypeptides.

As described in detail below, certain embodiments of the invention relate to human mesothelin polypeptides, which include polypeptides such as the novel soluble mesothelin related antigen (MRA) polypeptide described herein, and also include the cell surface-associated portion of mesothelin (Chang et al., 1996 *Proc. Nat. Acad. Sci. USA* 93:136) and the membrane bound portion of the megakaryocyte potentiating factor (MPF) precursor (Kojima et al., 1995 *J. Biol. Chem.* 270:21984). In certain other embodiments, the invention relates to fragments, derivatives and/or analogs of MRA polypeptides. Briefly, according to certain embodiments of the present invention, there is provided a method of screening for the presence of a malignant condition in a subject by contacting a biological sample from the subject with an antibody specific for a human mesothelin polypeptide. The complete amino acid and nucleic acid coding sequences of MRA are disclosed herein, including the surprising observation that a nucleic acid molecule derived from polyA+ RNA and which encodes MRA lacks a stop codon. The complete amino acid and nucleic acid coding sequences for mesothelin (Chang et al., 1996) and MPF (Kojima et al., 1995) are known, including the portions of those sequences corresponding to mesothelin polypeptides as used herein, including MRA.

Expression of mesothelin polypeptides in the cytoplasm as well as on the surfaces of a variety of human tumor cell lines is known (see e.g., Chang et al., 1996; Kojima et al., 1995; and references cited therein), which permits the use of such cells as immunogens for generating antibodies specific for a mesothelin polypeptide, as described herein. A monoclonal antibody that specifically recognizes a human mesothelin polypeptide has been reported and is available (Chang et al., 1996; Chang et al., 1992 *Int. J. Cancer* 50:373). Alternatively, those having ordinary skill in the art may routinely and without undue experimentation immunize a host and screen for mesothelin polypeptide specific antibody production using the present teachings along with methodologies well known in the art. For example, certain tumor cells that may be used as immunogens are known to express mesothelin polypeptides (see e.g., Chang et al., 1996; Kojima et al., 1995; and references cited therein), and determination of mesothelin polypeptide expression in a candidate immunogenic cell line can be accomplished based upon characterization of mesothelin polypeptides provided herein and/or upon detectable expression of the nucleotide sequences encoding mesothelin polypeptides as reported, for example, in Chang et al. (1996) and Kojima et al. (1995).

From the physicochemical and immunochemical properties of soluble mesothelin polypeptides disclosed herein, and using the presently disclosed nucleic acid sequences encoding members of the mesothelin polypeptide family that are mesothelin related antigens (MRAs), or optionally using the reported properties of nucleotide sequences encoding other mesothelin polypeptides (e.g., mesothelin or MPF), a person having ordinary skill in the art may also prepare a recombinant mesothelin polypeptide that can be used to produce and characterize specific antibodies according to well known methodologies. Mesothelin polypeptides can be expressed in mammalian cells, yeast, bacteria, or other cells under the control of appropriate promoters. Cell-free translation systems can also be employed to produce such proteins using RNAs derived from the mesothelin polypeptide DNA coding regions of the cited references (Chang et al., 1996; Kojima et al., 1995) or from the MRA-encoding nucleic acid sequences disclosed herein, or that can be deduced from MRA amino acid sequences provided herein. Appropriate cloning and expression vectors for use with prokaryotic and eukaryotic hosts are described by Sambrook et al., *Molecular Cloning: A Laboratory Manual*, Second Edition, Cold Spring Harbor, N.Y., (1989). In preferred embodiments of the invention, mesothelin polypeptides are expressed in mammalian cells.

The nucleic acids of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes an MRA polypeptide for use according to the invention may be identical to the coding sequence provided in SEQ ID NO:3 or in SEQ ID NO:4 or may be a different coding sequence, which, as a result of the redundancy or degeneracy of the genetic code, encodes the same MRA polypeptide as, for example, the cDNAs SEQ ID NOS:3 and 4. The present invention therefore provides an isolated nucleic acid molecule that encodes a mesothelin related antigen polypeptide having the amino acid sequence of SEQ ID NOS:1 or 2, or a nucleic acid molecule capable of hybridizing to such an MRA polypeptide-encoding nucleic acid, or a nucleic acid molecule having a sequence complementary thereto.

Variants preferably exhibit at least about 70% identity, more preferably at least about 80% identity and most preferably at least about 90% identity to a polynucleotide sequence that encodes a native mesothelin related antigen polypeptide or a portion thereof, such as, for example, the nucleic acid sequences set forth in SEQ ID NOS:3 and 4. The percent identity may be readily determined by comparing sequences using computer algorithms well known to those of ordinary skill in the art, such as Align or the BLAST algorithm (Altschul, *J. Mol. Biol.* 219:555-565, 1991; Henikoff and Henikoff, *Proc. Natl. Acad. Sci. USA* 89:10915-10919, 1992), which is available at the NCBI website (http://www/ncbi.nlm.nih.gov/cgi-bin/BLAST). Default parameters may be used.

Certain variants are substantially homologous to a native gene. Such polynucleotide variants are capable of hybridizing under moderately stringent conditions to a naturally occurring DNA or RNA sequence encoding a native mesothelin related antigen (or a complementary sequence). Suitable moderately stringent conditions include, for example, the following steps or their equivalent: prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS. For additional stringency, conditions may include, for example, a wash in 0.1×SSC and 0.1% SDS at 60° C. for 15 minutes, or the equivalent. A person having ordinary skill in the art will readily appreciate the parameters that may be varied as a routine matter to create appropriately stringent hybridization conditions that are in some way selective for a particular nucleic acid of interest, and will further appreciate that such conditions may be a function, inter alia, of the particular nucleic acid sequences involved in the hybridization, such as, for example, those disclosed herein as SEQ ID NOS:3 and 4, which encode mesothelin related antigen polypeptides MRA-1 and MRA-2, respectively. See also, e.g., Ausubel et al., *Current Protocols in Molecular Biology*, Greene Publishing, 1995, regarding selection of nucleic acid hybridization conditions.

The nucleic acids which encode MRA polypeptides, for example the human MRA polypeptides having the amino acid sequences of SEQ ID NOS:1-2 or any other MRA polypeptides for use according to the invention, may include, but are not limited to: only the coding sequence for the MRA polypeptide; the coding sequence for the MRA polypeptide and additional coding sequence; the coding sequence for the MRA polypeptide (and optionally additional coding sequence) and non-coding sequence, such as introns or non-coding sequences 5' and/or 3' of the coding sequence for the MRA polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding an MRA polypeptide" encompasses a nucleic acid which includes only coding sequence for the polypeptide as well as a nucleic acid which includes additional coding and/or non-coding sequence(s).

The present invention further relates to variants of the herein described nucleic acids which encode for fragments, analogs and derivatives of an MRA polypeptide, for example the human MRA polypeptides having the deduced amino acid sequences of SEQ ID NOS:1 and 2. The variants of the nucleic acids encoding MRAs may be naturally occurring allelic variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded MRA polypeptide. Thus, for example, the present invention includes nucleic acids encoding the same MRA polypeptides as shown in SEQ ID NOS:1 and 2, as well as variants of such nucleic acids, which variants may encode a fragment, derivative or analog of any of the polypeptides of SEQ ID NOS:1 or 2.

Variants and derivatives of MRA may be obtained by mutations of nucleotide sequences encoding MRA polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

Identification of nucleic acid molecules for use as antisense agents, which includes antisense oligonucleotides and ribozymes specific for nucleic acid sequences encoding MRA polypeptides or variants or fragments thereof; and of DNA oligonucleotides encoding MRA genes for targeted delivery for genetic therapy, involve methods well known in the art. For example, the desirable properties, lengths and other characteristics of such oligonucleotides are well known. In certain preferred embodiments such an antisense oligonucleotide comprises at least 15 consecutive nucleotides complementary to an isolated nucleic acid molecule encoding an MRA polypeptide as provided herein. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539-3542 (1987); Miller et al., *J. Am. Chem. Soc.* 93:6657-6665 (1971); Stec et al., *Tetrehedron Lett.* 26:2191-2194 (1985); Moody et al., *Nucl. Acids Res.* 12:4769-4782 (1989); Uznanski et al., *Nucl. Acids Res.* (1989); Letsinger et al., *Tetrahedron* 40:137-143 (1984); Eckstein, *Annu. Rev. Biochem.* 54:367-402 (1985); Eckstein, *Trends Biol. Sci.* 14:97-100 (1989); Stein In: *Oligodeoxynucleotides. Antisense Inhibitors of Gene Expression*, Cohen, Ed, Macmillan Press, London, pp. 97-117 (1989); Jager et al., *Biochemistry* 27:7237-7246 (1988)).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucl. Acids Res.* 21:3405-3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

According to this embodiment of the invention, particularly useful antisense nucleotides and triplex molecules are molecules that are complementary to or bind the sense strand of DNA or mRNA that encodes an MRA polypeptide such that inhibition of translation of mRNA encoding the MRA polypeptide is effected.

A ribozyme is an RNA molecule that specifically cleaves RNA substrates, such as mRNA, resulting in specific inhibition or interference with cellular gene expression. There are at least five known classes of ribozymes involved in the cleavage and/or ligation of RNA chains. Ribozymes can be targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116, 742 and 5,093,246 to Cech et al.). According to certain embodiments of the invention, any such MRA mRNA-specific ribozyme, or a nucleic acid encoding such a ribozyme, may be delivered to a host cell to effect inhibition of MRA gene expression. Ribozymes, and the like may therefore be delivered to the host cells by DNA encoding the ribozyme linked to a eukaryotic promoter, such as a eukaryotic viral promoter, such that upon introduction into the nucleus, the ribozyme will be directly transcribed.

Equivalent DNA constructs that encode various additions or substitutions of amino acid residues or sequences, or deletions of terminal or internal residues or sequences not needed for biological activity are also encompassed by the invention. For example, sequences encoding Cys residues that are not essential for biological activity can be altered to cause the Cys residues to be deleted or replaced with other amino acids, preventing formation of incorrect intramolecular disulfide bridges upon renaturation. Other equivalents can be prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

The appropriate DNA sequence(s) may be inserted into any of a number of well known vectors appropriate for the selected host cell by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); and elsewhere.

Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived, for example, from SV40 splice and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

The present invention further relates to MRAs, to mesothelin related antigen polypeptides and in particular to methods for detecting a malignant condition. In a preferred embodiment, malignancy is detected by determining the presence in a biological sample of a naturally occurring soluble molecule having an antigenic determinant reactive with at least one antibody specific for a human mesothelin polypeptide. In another preferred embodiment, malignancy is detected by determining the presence in a biological sample of at least one naturally occurring MRA polypeptide. As provided herein, a "mesothelin related antigen polypeptide" or "MRA polypeptide" includes any polypeptide having an amino acid sequence of SEQ ID NO:1 or 2, including any fragment, derivative or analog thereof, and also includes any polypeptide encoded by a nucleic acid molecule comprising SEQ ID NO:3 or 4, or by a nucleic acid molecule capable of hybridizing to a nucleic acid molecule of SEQ ID NO:3 or 4, or a fragment, derivative or analog thereof. Therefore, depending on the portion of a presently disclosed MRA amino acid or nucleic acid sequence that is selected, an MRA polypeptide may, but need not, be a mesothelin polypeptide. As provided herein, a "mesothelin polypeptide" is a soluble polypeptide having an amino acid sequence that includes the peptide:

EVEKTACPSGKKAREIDES SEQ ID NO:5 and further having at least one antigenic determinant reactive with at least one antibody having an antigen combining site that competitively inhibits the immunospecific binding of MAb K-1 (Chang et al., 1996 *Proc. Nat. Acad. Sci. USA* 93:136; MAb K-1 is available from, e.g., Signet Laboratories, Inc., Dedham, Mass.) or of monoclonal antibodies OV569, 4H3, 3G3 or 1A6 as provided herein. A mesothelin polypeptide may include, for example, a mesothelin related antigen (A) polypeptide as provided herein, or may be derived from the cell surface associated portion of mesothelin itself (Chang et al., 1996), the membrane bound portion of the MPF precursor protein (Kojima et al., 1995 *J. Biol. Chem.* 270:21984), or any fragments, analogs and derivatives of such polypeptides.

The MRA polypeptide or the mesothelin polypeptide of the invention may be an unmodified polypeptide or may be a polypeptide that has been posttranslationally modified, for example by glycosylation, phosphorylation, fatty acylation including glycosylphosphatidylinositol anchor modification or the like, phospholipase cleavage such as phosphatidylinositol-specific phospholipase c mediated hydrolysis or the like, protease cleavage, dephosphorylation or any other type of protein posttranslational modification such as a modification involving formation or cleavage of a covalent chemical bond.

The terms "fragment," "derivative" and "analog" when referring to mesothelin related antigen polypeptides or fusion proteins, refers to any mesothelin related antigen polypeptide that retains essentially the same biological function and/or activity as such polypeptide. Thus, an analog may include a mesothelin related antigen polypeptide isoform such as a differentially posttranslationally modified mesothelin related antigen polypeptide or a variant such as a splice variant. As is well known in the art, a "splice variant" includes variant or alternative forms of a polypeptide that arise from the differential intracellular processing of an RNA transcript. For example, two distinct mRNA species may be splice variants of one another where they differ only by the inclusion of all or a portion of a sequence corresponding to a particular exon in one mRNA species and its absence from the other species. As those familiar with the art will appreciate, other structural relationships can exist between mRNA species that would be generally regarded as splice variants. A mesothelin polypeptide further includes a proprotein which can be activated by cleavage of the proprotein portion to produce an active mesothelin polypeptide.

Biological functions and/or activities of fragments, derivatives and analogs of MRA polypeptides or of mesothelin polypeptides include, but need not be limited to, the use of such polypeptides as markers in a method of screening for the presence of a malignant condition in a subject as disclosed herein. For example, by detecting in a sample from the subject a molecule naturally occurring in soluble form and having an antigenic determinant that is reactive with at least one antibody specific for a mesothelin polypeptide, one skilled in the art may be monitoring a biological function and/or activity of an MRA polypeptide and/or of a mesothelin polypeptide. Further, it should be noted that in certain embodiments the subject invention method of screening is directed to comparing relative quantities, levels and/or amounts of a detectable molecule naturally occurring in soluble form and having an antigenic determinant that is reactive with at least one antibody specific for a mesothelin polypeptide in each of (i) a first biological sample from a first subject suspected of having a malignant condition, and (ii) a second biological sample from a second subject known to be free of a malignant condition. Accordingly, the relative quantitative presence of a mesothelin polypeptide in a biological sample may be a biological function and/or activity of a mesothelin polypeptide, although such function and/or activity should not be so limited.

A fragment, derivative or analog of a MRA polypeptide or a mesothelin polypeptide may be (i) one in which one or more of the amino acid residues are substituted with a conserved or non-conserved amino acid residue (preferably a conserved amino acid residue); (ii) one in which additional amino acids are fused to the mesothelin polypeptide, including amino acids that may be employed for purification of the mesothelin polypeptide or a proprotein sequence; or (iii) a truncated mesothelin polypeptide. Such fragments, derivatives and analogs are deemed to be within the scope of those skilled in the art from the teachings herein.

A truncated mesothelin polypeptide may be any mesothelin polypeptide molecule that comprises less than a full length version of the mesothelin polypeptide. Truncated molecules provided by the present invention may include truncated biological polymers, and in preferred embodiments of the invention such truncated molecules may be truncated nucleic acid molecules or truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule. Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences. In other preferred embodiments, truncated molecules are polypeptides that comprise less than the full length amino acid sequence of a particular protein.

As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1-1500 contiguous nucleotide or amino acid residues, preferably 1-500 contiguous nucleotide or amino acid residues and more preferably 1-300 contiguous nucleotide or amino acid residues.

As known in the art "similarity" between two polypeptides is determined by comparing the amino acid sequence and conserved amino acid substitutes thereto of the polypeptide to the sequence of a second polypeptide. Similarity between two polypeptide or nucleotide sequences, or even the percent identity, may be readily determined by comparing sequences using computer algorithms well known to those of ordinary skill in the art, such as the BLAST algorithm (Altschul, *J. Mol. Biol.* 219:555-565, 1991; Henikoff and Henikoff, *Proc. Natl. Acad. Sci. USA* 89:10915-10919, 1992), which is available at the NCBI website (http://www/ncbi.nlm.nih.gov/cgi-bin/BLAST). Default parameters may be used. Examples of other useful computer algorithms are those used in programs such as Align and FASTA, which may be accessed, for example, at the Genestream internet website of the Institut de Genetique Humaine, Montpellier, France (www2.igh.cnrs.fr/home.eng.html) and used with default parameters. Fragments or portions of the polypeptides of the present invention may be employed for producing the corresponding full-length polypeptide by peptide synthesis; therefore, the fragments may be employed as intermediates for producing the full-length polypeptides.

The term "isolated" means that the material is removed from its original environment (e.g., the natural environment if it is naturally occurring). For example, a naturally occurring polypeptide or polynucleotide present in a living animal is not isolated, but the same polypeptide or polynucleotide, separated from some or all of the co-existing materials in the natural system, is isolated. Such polypeptides or polynucleotides could be part of a composition, and still be isolated in that such composition is not part of its natural environment.

Affinity techniques are particularly useful in the context of isolating MRA polypeptides and/or mesothelin polypeptides for use according to the methods of the present invention, and may include any method that exploits a specific binding interaction with a MRA polypeptide or mesothelin polypeptide to effect a separation. For example, because mesothelin polypeptides may contain covalently attached oligosaccharide moieties (see, e.g., Chang et al., 1996 *Proc. Nat. Acad. Sci. USA* 93:136; Chang et al., 1992 *Cancer Res.* 52:181; Kojima et al., 1995 *J. Biol Chem.* 270:21984; Yamaguchi et al., 1994 *J. Biol. Chem.* 269:805), an affinity technique such as binding of a mesothelin polypeptide to a suitable immobilized lectin under conditions that permit carbohydrate binding by the lectin may be a particularly useful affinity technique. Other useful affinity techniques include immunological techniques for isolating a mesothelin polypeptide, which techniques rely on specific binding interaction between antibody combining sites for antigen and antigenic determinants present in the complexes. Immunological techniques include, but need not be limited to, immunoaffinity chromatography, immunoprecipitation, solid phase immunoadsorption or other immunoaffinity methods. For these and other useful affinity techniques, see, for example, Scopes, R. K., *Protein Purification: Principles and Practice,* 1987, Springer-Verlag, N.Y.; Weir, D. M., *Handbook of Experimental Immunology,* 1986, Blackwell Scientific, Boston; and Hermanson, G. T. et al., *Immobilized Affinity Ligand Techniques,* 1992, Academic Press, Inc., California; which are hereby incorporated by reference in their entireties, for details regarding techniques for isolating and characterizing complexes, including affinity techniques.

As described herein, the invention provides a fusion protein comprising a polypeptide fused to a MRA. Such MRA fusion proteins are encoded by nucleic acids that have the MRA coding sequence fused in frame to an additional coding sequence to provide for expression of a MRA polypeptide sequence fused to an additional functional or non-functional polypeptide sequence that permits, for example by way of illustration and not limitation, detection, isolation and/or purification of the MRA fusion protein. Such MRA fusion proteins may permit detection, isolation and/or purification of the MRA fusion protein by protein-protein affinity, metal affinity or charge affinity-based polypeptide purification, or by specific protease cleavage of a fusion protein containing a fusion sequence that is cleavable by a protease such that the MRA polypeptide is separable from the fusion protein.

Thus, MRA fusion proteins may comprise affinity tag polypeptide sequences, which refers to polypeptides or peptides added to MRA to facilitate detection and isolation of the MRA via a specific affinity interaction with a ligand. The ligand may be any molecule, receptor, counterreceptor, antibody or the like with which the affinity tag may interact through a specific binding interaction as provided herein. Such peptides include, for example, poly-His or the antigenic identification peptides described in U.S. Pat. No. 5,011,912 and in Hopp et al., (1988 *Bio/Technology* 6:1204), or the XPRESS™ epitope tag (Invitrogen, Carlsbad, Calif.). The affinity sequence may be a hexa-histidine tag as supplied, for example, by a pBAD/His (Invitrogen) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37:767).

MRA fusion proteins may further comprise immunoglobulin constant region polypeptides added to MRA to facilitate detection, isolation and/or localization of A. The immunoglobulin constant region polypeptide preferably is fused to the C-terminus of a MRA polypeptide. General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990). A gene fusion encoding the MRA:Fc fusion protein is inserted into an appropriate expression vector. In certain embodiments of the invention, MRA:Fc fusion proteins may be allowed to assemble much like antibody molecules, whereupon interchain disulfide bonds form between Fc polypeptides, yielding dimeric MRA fusion proteins.

MRA fusion proteins having specific binding affinities for pre-selected antigens by virtue of fusion polypeptides comprising immunoglobulin V-region domains encoded by DNA sequences linked in-frame to sequences encoding MRA are also within the scope of the invention, including variants and fragments thereof as provided herein. General strategies for the construction of fusion proteins having immunoglobulin V-region fusion polypeptides are disclosed, for example, in EP 0318554; U.S. Pat. No. 5,132,405; U.S. Pat. No. 5,091,513; and U.S. Pat. No. 5,476,786.

The nucleic acid of the present invention may also encode a fusion protein comprising a MRA polypeptide fused to other polypeptides having desirable affinity properties, for example an enzyme such as glutathione-S-transferase. As another example, MRA fusion proteins may also comprise a MRA polypeptide fused to a *Staphylococcus aureus* protein A polypeptide; protein A encoding nucleic acids and their use in constructing fusion proteins having affinity for immunoglobulin constant regions are disclosed generally, for example, in U.S. Pat. No. 5,100,788. Other useful affinity polypeptides for construction of MRA fusion proteins may include streptavidin fusion proteins, as disclosed, for example, in WO 89/03422; U.S. Pat. No. 5,489,528; U.S. Pat. No. 5,672,691; WO 93/24631; U.S. Pat. No. 5,168,049; U.S. Pat. No. 5,272,254 and elsewhere, and avidin fusion proteins (see, e.g., EP 511,747). As provided herein and in the cited references, MRA polypeptide sequences, including substrate trapping mutant MRAs, may be fused to fusion polypeptide sequences that may be full length fusion polypeptides and that may alternatively be variants or fragments thereof.

The present invention also contemplates MRA fusion proteins that contain polypeptide sequences that direct the fusion protein to the cell nucleus, to reside in the lumen of the endoplasmic reticulum (ER), to be secreted from a cell via the classical ER-Golgi secretory pathway (see, e.g., von Heijne, *J. Membrane Biol.* 115:195-201, 1990), to be incorporated into the plasma membrane, to associate with a specific cytoplasmic component including the cytoplasmic domain of a transmembrane cell surface receptor or to be directed to a particular subcellular location by any of a variety of known intracellular protein sorting mechanisms with which those skilled in the art will be familiar (See, e.g., Rothman, *Nature* 372:55-63, 1994, Adrani et al., 1998 *J. Biol. Chem.* 273: 10317, and references cited therein.). Accordingly, these and related embodiments are encompassed by the instant compositions and methods directed to targeting a polypeptide of interest to a predefined intracellular, membrane or extracellular localization.

The present invention also relates to vectors and to constructs that include nucleic acids of the present invention, and in particular to "recombinant expression constructs" that include any nucleic acids encoding MRA polypeptides according to the invention as provided above; to host cells which are genetically engineered with vectors and/or constructs of the invention and to the production of MRA polypeptides and fusion proteins of the invention, or fragments or variants thereof, by recombinant techniques. MRA proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described, for example, by Sambrook, et al., *Molecular Cloning: A Laboratory Manual*, Second Edition, Cold Spring Harbor, N.Y. (1989).

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression constructs for bacterial use are constructed by inserting into an expression vector a structural DNA sequence encoding a desired protein together with suitable translation initiation and termination signals in operable reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. Any other plasmid or vector may be used as long as they are replicable and viable in the host.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter, if it is a regulated promoter as provided herein, is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well know to those skilled in the art.

Thus, for example, the nucleic acids of the invention as provided herein may be included in any one of a variety of expression vector constructs as a recombinant expression construct for expressing a MRA polypeptide. Such vectors and constructs include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA, such as vaccinia, adenovirus, fowl pox virus, and pseudorabies. However, any other vector may be used for preparation of a recombinant expression construct as long as it is replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the expression vector is operatively linked to at least one appropriate expression control sequences (e.g., a promoter or a regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding a MRA polypeptide is described herein.

As noted above, in certain embodiments the vector may be a viral vector such as a retroviral vector. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, 1:5-14 (1990), which is incorporated herein by reference in its entirety. The vector may transduce the packaging cells through any means known in the art. Such means include, but are not limited to, electroporation, the use of liposomes, and calcium phosphate precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the MRA polypeptides or fusion proteins. Such retroviral vector particles then may be employed, to transduce eukaryotic cells, either in vitro or in vivo. The transduced eukaryotic cells will express the nucleic acid sequence(s) encoding the MRA polypeptide or fusion protein. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, bronchial epithelial cells and various other culture-adapted cell lines.

As another example of an embodiment of the invention in which a viral vector is used to prepare the recombinant MRA expression construct, in one preferred embodiment, host cells transduced by a recombinant viral construct directing the expression of MRA polypeptides or fusion proteins may produce viral particles containing expressed MRA polypeptides or fusion proteins that are derived from portions of a host cell membrane incorporated by the viral particles during viral budding. In another preferred embodiment, MRA encoding nucleic acid sequences are cloned into a baculovirus shuttle vector, which is then recombined with a baculovirus to generate a recombinant baculovirus expression construct that is used to infect, for example, Sf9 host cells, as described in *Baculovirus Expression Protocols, Methods in Molecular Biology* Vol. 39, C. D. Richardson, Editor, Human Press, Totowa, N.J., 1995; Piwnica-Worms, "Expression of Proteins in Insect Cells Using Baculoviral Vectors," Section II in Chapter 16 in: *Short Protocols in Molecular Biology*, 2nd Ed., Ausubel et al., eds., John Wiley & Sons, New York, N.Y., 1992, pages 16-32 to 16-48.

In another aspect, the present invention relates to host cells containing the above described recombinant MRA expression constructs. Host cells are genetically engineered (transduced, transformed or transfected) with the vectors and/or expression constructs of this invention which may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding MRA polypeptides or MRA fusion proteins. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli*, Streptomyces, *Salmonella typhimurium*; fungal cells, such as yeast; insect cells, such as *Drosophila* S2 and Spodoptera Sf9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. The invention is therefore directed in part to a method of producing a recombinant MRA polypeptide, by culturing a host cell comprising a recombinant expression construct that comprises at least one promoter operably linked to a nucleic acid sequence encoding a MRA. In certain embodiments, the promoter may be a regulated promoter as provided herein, for example a tetracylcine-repressible promoter. In certain embodiments the recombinant expression construct is a recombinant viral expression construct as provided herein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of MRA expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

The expressed recombinant mesothelin related antigen polypeptides (or mesothelin polypeptides), or fusion proteins derived therefrom, may be useful as immunogens in the form of intact host cells; intact organelles such as cell membranes, intracellular vesicles or other cellular organelles; or disrupted cell preparations including but not limited to cell homogenates or lysates, uni- and multilamellar membrane vesicles or other preparations. Alternatively, expressed recombinant mesothelin related antigen polypeptides (or mesothelin polypeptides) or fusion proteins can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography including immunoaffinity chromatography, hydroxylapatite chromatography and lectin chromatography. Protein refolding steps can be used, as necessary, in completing configuration of the mature protein. Finally, high performance liquid chromatography (HPLC) can be employed for final purification steps. Expressed recombinant mesothelin related antigen polypeptides (or mesothelin polypeptides) or fusion proteins may also be useful as target antigens in any of a number of assay configurations for routine antibody screening, which can be readily performed by those having ordinary skill in the art.

The mesothelin related antigen polypeptide (or mesothelin polypeptide) that is an immunogen for the production of a specific antibody to be used in the method of the present invention may thus be a naturally purified product, or a product of chemical synthetic procedures, or produced by recombinant techniques from a prokaryotic or, preferably, a eukaryotic host. Depending upon the host employed in a recombinant production procedure, the polypeptides of the present invention may be glycosylated or otherwise post-translationally modified as known in the art and as provided herein.

According to the present invention, a soluble human mesothelin related antigen polypeptide (or mesothelin polypeptide) may be detected in a biological sample from a subject or biological source. Biological samples may be provided by obtaining a blood sample, biopsy specimen, tissue explant, organ culture, biological fluid or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. In certain preferred embodiments of the invention, the subject or biological source may be suspected of having or being at risk for having a malignant condition, and in certain preferred embodiments of the invention the subject or biological source may be known to be free of a risk or presence of such disease.

In preferred embodiments the biological sample is a biological fluid containing a soluble human mesothelin related antigen polypeptide. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, cerebrospinal fluid, saliva, mucosal secretions of the secretory tissues and organs, vaginal secretions, ascites fluids such as those associated with non-solid tumors, fluids of the pleural, pericardial, peritoneal, abdominal and other body cavities, and the like. Biological fluids may also include liquid solutions contacted with a subject or biological source, for example, cell and organ culture medium including cell or organ conditioned medium, lavage fluids and the like. In certain highly preferred embodiments the biological sample is serum, and in certain other highly preferred embodiments the biological sample is plasma. In other preferred embodiments the biological sample is a cell-free liquid solution.

In certain other preferred embodiments the biological sample comprises an intact cell, and in certain other preferred embodiments the biological sample comprises a cell extract containing a nucleic acid sequence encoding a mesothelin related antigen polypeptide having the amino acid sequence set forth in SEQ ID NOS:1 or 2, or a fragment or variant thereof.

A "molecule naturally occurring in soluble form" in a sample may be a soluble protein, polypeptide; peptide, amino acid, or derivative thereof; a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like; or any combination thereof such as, for example, a glycoprotein, a glycolipid, a lipoprotein, a proteolipid, or any other biological molecule that is a soluble or cell-free constituent of a biological sample as provided herein. A "molecule naturally occurring in soluble form" further refers to a molecule that is in solution or present in a biological sample, including a biological fluid as provided herein, and that is not bound to the surface of an intact cell. For example, a molecule naturally occurring in soluble form may include but need not be limited to a solute; a component of a macromolecular complex; a material that is shed, secreted or exported from a cell; a colloid; a microparticle or nanoparticle or other fine suspension particle; or the like.

The presence of a malignant condition in a subject refers to the presence of dysplastic, cancerous and/or transformed cells in the subject, including, for example neoplastic, tumor, non-contact inhibited or oncogenically transformed cells, or the like. By way of illustration and not limitation, in the context of the present invention a malignant condition may refer further to the presence in a subject of cancer cells that are capable of secreting, shedding, exporting or releasing a mesothelin related antigen polypeptide (or a mesothelin polypeptide) in such a manner that elevated levels of such a polypeptide are detectable in a biological sample from the subject. In preferred embodiments, for example, such cancer cells are malignant epithelial cells such as carcinoma cells, and in particularly preferred embodiments such cancer cells are malignant mesothelioma cells, which are transformed variants of squamous cell epithelial or mesothelial cells that are found, for example, lining pleural, pericardial, peritoneal, abdominal and other body cavities.

In the most preferred embodiments of the invention, tumor cells, the presence of which signifies the presence of a malignant condition, are ovarian carcinoma cells, including primary and metastatic ovarian carcinoma cells. Criteria for classifying a malignancy as ovarian carcinoma are well known in the art (see, e.g., Bell et al., 1998 *Br. J. Obstet. Gynaecol.* 105:1136; Meier et al., 1997 *Anticancer Res.* 17(4B):3019; Meier et al. 1997 *Anticancer Res.* 17(4B):2949; Cioffi et al., 1997 Tumori 83:594; and references cited therein) as are the establishment and characterization of human ovarian carcinoma cell lines from primary and metastatic tumors (e.g., OVCAR-3, Amer. Type Culture Collection, Manassas, Va.; Yuan et al., 1997 *Gynecol. Oncol.* 66:378). In other embodiments, the malignant condition may be mesothelioma, pancreatic carcinoma, non-small cell lung carcinoma or another form of cancer, including any of the various carcinomas such as squamous cell carcinomas and adenocarcinomas, and also including sarcomas and hematologic malignancies (e.g., leukemias, lymphomas, myelomas, etc.). Classification of these and other malignant conditions is known to those having familiarity with the art, and the present disclosure provides determination of the presence of a mesothelin polypeptide, including determination of the presence of a MRA polypeptide, in such a malignant condition without undue experimentation.

As provided herein, the method of screening for the presence of a malignant condition in a subject may feature the use of an antibody specific for a human mesothelin related antigen polypeptide or an antibody specific for a human mesothelin polypeptide.

Antibodies that are specific for a mesothelin related antigen polypeptide (or a mesothelin polypeptide) are readily generated as monoclonal antibodies or as polyclonal antisera, or may be produced as genetically engineered immunoglobulins (Ig) that are designed to have desirable properties using methods well known in the art. For example, by way of illustration and not limitation, antibodies may include recombinant IgGs, chimeric fusion proteins having immunoglobulin derived sequences or "humanized" antibodies (see, e.g., U.S. Pat. Nos. 5,693,762; 5,585,089; 4,816,567; 5,225,539; 5,530,101; and references cited therein) that may all be used for detection of a human mesothelin polypeptide according to the invention. Many such antibodies have been disclosed and are available from specific sources or may be prepared as provided herein, including by immunization with mesothelin polypeptides as described below. For example, as provided herein, nucleic acid sequences encoding mesothelin polypeptides are known for the cell surface associated portion of mesothelin itself (Chang et al., 1996) and for the membrane bound portion of the megakaryocyte potentiating factor (MPF) precursor protein (Kojima et al., 1995), and the present disclosure further provides nucleic acid sequences encoding mesothelin related antigen (MRA) polypeptides, such that those skilled in the art may routinely prepare these polypeptides for use as immunogens. For instance, monoclonal antibodies such as 4H3, 3G3 and 1A6, which are described in greater detail below, may be used to practice certain methods according to the present invention. As also discussed above, another useful antibody is MAb K-1, a monoclonal antibody reactive with a mesothelin polypeptide (Chang et al., 1996 *Proc. Nat. Acad. Sci. USA* 93:136; Chang et al., 1992 *Int. J Cancer* 50:373; MAb K-1 is available from, e.g., Signet Laboratories, Inc., Dedham, Mass.).

The term "antibodies" includes polyclonal antibodies, monoclonal antibodies, fragments thereof such as $F(ab')_2$, and Fab fragments, as well as any naturally occurring or recombinantly produced binding partners, which are molecules that specifically bind a mesothelin polypeptide, for example mesothelin, mesothelin related antigen (MRA) or MPF. Antibodies are defined to be "immunospecific" or specifically binding if they bind a mesothelin polypeptide with a $K_a$ of greater than or equal to about $10^4 \text{ M}^{-1}$, preferably of greater than or equal to about $10^5 \text{ M}^{-1}$, more preferably of greater than or equal to about $10^6 \text{ M}^{-1}$ and still more preferably of greater than or equal to about $10^7 \text{ M}^{-1}$. Affinities of binding partners or antibodies can be readily determined using conventional techniques, for example those described by Scatchard et al., *Ann. N.Y. Acad. Sci.* 51:660 (1949). Determination of other proteins as binding partners of a mesothelin polypeptide can be performed using any of a number of known methods for identifying and obtaining proteins that specifically interact with other proteins or polypeptides, for example, a yeast two-hybrid screening system such as that described in U.S. Pat. No. 5,283,173 and U.S. Pat. No. 5,468,614, or the equivalent. The present invention also includes the use of a mesothelin polypeptide, and peptides based on the amino acid sequence of a mesothelin polypeptide, to prepare binding partners and antibodies that specifically bind to a mesothelin polypeptide.

Antibodies may generally be prepared by any of a variety of techniques known to those of ordinary skill in the art (see, e.g., Harlow and Lane, *Antibodies: A Laboratory Manual*, Cold Spring Harbor Laboratory, 1988). In one such technique, an immunogen comprising a mesothelin polypeptide, for example a cell having a mesothelin polypeptide on its surface or an isolated mesothelin polypeptide such as mesothelin, MRA or MPF, is initially injected into a suitable animal (e.g., mice, rats, rabbits, sheep and goats), preferably according to a predetermined schedule incorporating one or more booster immunizations, and the animals are bled periodically. Polyclonal antibodies specific for the mesothelin polypeptide may then be purified from such antisera by, for example, affinity chromatography using the polypeptide coupled to a suitable solid support.

Monoclonal antibodies specific for mesothelin polypeptides or variants thereof may be prepared, for example, using the technique of Kohler and Milstein (1976 Eur. J. Immunol. 6:511-519), and improvements thereto. Briefly, these methods involve the preparation of immortal cell lines capable of producing antibodies having the desired specificity (i.e., reactivity with the mesothelin polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a membrane fusion promoting agent such as polyethylene glycol or a nonionic detergent for a few minutes, and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred. Hybridomas that generate monoclonal antibodies that specifically bind to mesothelin polypeptides are contemplated by the present invention.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. For example, antibodies may be purified by chromatography on immobilized Protein G or Protein A using standard techniques.

Within certain embodiments, the use of antigen-binding fragments of antibodies may be preferred. Such fragments include Fab fragments, which may be prepared using standard techniques (e.g., by digestion with papain to yield Fab and Fc fragments). The Fab and Fc fragments may be separated by affinity chromatography (e.g., on immobilized protein A columns), using standard techniques. See, e.g., Weir, D. M., Handbook of Experimental Immunology, 1986, Blackwell Scientific, Boston.

Multifunctional fusion proteins having specific binding affinities for pre-selected antigens by virtue of immunoglobulin V-region domains encoded by DNA sequences linked in-frame to sequences encoding various effector proteins are known in the art, for example, as disclosed in EP-B1-0318554, U.S. Pat. No. 5,132,405, U.S. Pat. No. 5,091,513 and U.S. Pat. No. 5,476,786. Such effector proteins include polypeptide domains that may be used to detect binding of the fusion protein by any of a variety of techniques with which those skilled in the art will be familiar, including but not limited to a biotin mimetic sequence (see, e.g., Luo et al., 1998 J. Biotechnol. 65:225 and references cited therein), direct covalent modification with a detectable labeling moiety, non-covalent binding to a specific labeled reporter molecule, enzymatic modification of a detectable substrate or immobilization (covalent or non-covalent) on a solid-phase support.

Single chain antibodies for use in the present invention may also be generated and selected by a method such as phage display (see, e.g., U.S. Pat. No. 5,223,409; Schlebusch et al., 1997 Hybridoma 16:47; and references cited therein). Briefly, in this method, DNA sequences are inserted into the gene III or gene VIII gene of a filamentous phage, such as M13. Several vectors with multicloning sites have been developed for insertion (McLafferty et al., Gene 128:29-36, 1993; Scott and Smith, Science 249:386-390, 1990; Smith and Scott, Methods Enzymol. 217:228-257, 1993). The inserted DNA sequences may be randomly generated or may be variants of a known binding domain for binding to a mesothelin polypeptide. Single chain antibodies may readily be generated using this method. Generally, the inserts encode from 6 to 20 amino acids. The peptide encoded by the inserted sequence is displayed on the surface of the bacteriophage. Bacteriophage expressing a binding domain for a mesothelin polypeptide are selected by binding to an immobilized mesothelin polypeptide, for example a recombinant polypeptide prepared using methods well known in the art and nucleic acid coding sequences as disclosed by Chang et al. (1996 Proc. Nat. Acad. Sci. USA 93:136) or by Kojima et al. (1995 J. Biol. Chem. 270:21984). Unbound phage are removed by a wash, typically containing 10 mM Tris, 1 mM EDTA, and without salt or with a low salt concentration. Bound phage are eluted with a salt containing buffer, for example. The NaCl concentration is increased in a step-wise fashion until all the phage are eluted. Typically, phage binding with higher affinity will be released by higher salt concentrations. Eluted phage are propagated in the bacteria host. Further rounds of selection may be performed to select for a few phage binding with high affinity. The DNA sequence of the insert in the binding phage is then determined. Once the predicted amino acid sequence of the binding peptide is known, sufficient peptide for use herein as an antibody specific for a human mesothelin polypeptide may be made either by recombinant means or synthetically. Recombinant means are used when the antibody is produced as a fusion protein. The peptide may also be generated as a tandem array of two or more similar or dissimilar peptides, in order to maximize affinity or binding.

To detect an antigenic determinant reactive with an antibody specific for a human mesothelin polypeptide, the detection reagent is typically an antibody, which may be prepared as described herein. There are a variety of assay formats known to those of ordinary skill in the art for using an antibody to detect a polypeptide in a sample, including but not limited to enzyme linked immunosorbent assay (ELISA), radioimmunoassay (RIA), immunofluorimetry, immunoprecipitation, equilibrium dialysis, immunodiffusion and other techniques. See, e.g., Harlow and Lane, Antibodies: A Laboratory Manual, Cold Spring Harbor Laboratory, 1988; Weir, D. M., Handbook of Experimental Immunology, 1986, Blackwell Scientific, Boston. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as is well known in the art and described below.

In another embodiment, the assay involves the use of an antibody immobilized on a solid support to bind to the target mesothelin polypeptide and remove it from the remainder of the sample. The bound mesothelin polypeptide may then be detected using a second antibody reactive with a distinct mesothelin polypeptide antigenic determinant, for example, a reagent that contains a detectable reporter moiety. As a non-limiting example, according to this embodiment the immobilized antibody and the second antibody which recognize distinct antigenic determinants may be any two of the monoclonal antibodies described herein selected from the monoclonal antibodies OV569, 4H3, 3G3 and 1A6. Alternatively, a competitive assay may be utilized, in which a mesothelin polypeptide is labeled with a detectable reporter moiety and allowed to bind to the immobilized mesothelin polypeptide specific antibody after incubation of the immobilized antibody with the sample. The extent to which components of the sample inhibit the binding of the labeled polypeptide to the antibody is indicative of the reactivity of the sample with the immobilized antibody, and as a result, indicative of the level of mesothelin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain preferred embodiments, the assay for detection of mesothelin related antigen polypeptide in a sample is a two-antibody sandwich assay. This assay may be performed by first contacting a mesothelin related antigen polypeptide-specific antibody (e.g., a monoclonal antibody such as OV569, 1A6, 3G3 or 4H3) that has been immobilized on a solid support, commonly the well of a microtiter plate, with the biological sample, such that a soluble molecule naturally occurring in the sample and having an antigenic determinant that is reactive with the antibody is allowed to bind to the immobilized antibody (e.g., a 30 minute incubation time at room temperature is generally sufficient) to form an antigen-antibody complex or an immune complex. Unbound constituents of the sample are then removed from the immobilized immune complexes. Next, a second antibody specific for a mesothelin related antigen polypeptide is added, wherein the antigen combining site of the second antibody does not competitively inhibit binding of the antigen combining site of the immobilized first antibody to a mesothelin related antigen polypeptide (e.g., a monoclonal antibody such as OV569, 1A6, 3G3 or 4H3 that is not the same as the monoclonal antibody immobilized on the solid support). The second antibody may be detectably labeled as provided herein, such that it may be directly detected. Alternatively, the second antibody may be indirectly detected through the use of a detectably labeled secondary (or "second stage") anti-antibody, or by using a specific detection reagent as provided herein. The subject invention method is not limited to any particular detection procedure, as those having familiarity with immunoassays will appreciate that there are numerous reagents and configurations for immunologically detecting a particular antigen (e.g., a mesothelin polypeptide) in a two-antibody sandwich immunoassay.

In certain preferred embodiments of the invention using the two-antibody sandwich assay described above, the first, immobilized antibody specific for a mesothelin related antigen polypeptide is a polyclonal antibody and the second antibody specific for a mesothelin related antigen polypeptide is a polyclonal antibody. In certain other embodiments of the invention the first, immobilized antibody specific for a mesothelin related antigen polypeptide is a monoclonal antibody and the second antibody specific for a mesothelin related antigen polypeptide is a polyclonal antibody. In certain other embodiments of the invention the first, immobilized antibody specific for a mesothelin related antigen polypeptide is a polyclonal antibody and the second antibody specific for a mesothelin related antigen polypeptide is a monoclonal antibody. In certain other highly preferred embodiments of the invention the first, immobilized antibody specific for a mesothelin related antigen polypeptide is a monoclonal antibody and the second antibody specific for a mesothelin related antigen polypeptide is a monoclonal antibody. For example, in these embodiments it should be noted that monoclonal antibodies 4H3, 3G3, 1A6 and OV569 as provided herein recognize distinct and non-competitive antigenic determinants (e.g., epitopes) on mesothelin polypeptides such as MRA polypeptides, such that any pairwise combination of these monoclonal antibodies may be employed. In other preferred embodiments of the invention the first, immobilized antibody specific for a mesothelin related antigen polypeptide and/or the second antibody specific for a mesothelin related antigen polypeptide may be any of the kinds of antibodies known in the art and referred to herein, for example by way of illustration and not limitation, Fab fragments, F(ab')$_2$ fragments, immunoglobulin V-region fusion proteins or single chain antibodies. Those familiar with the art will appreciate that the present invention encompasses the use of other antibody forms, fragments, derivatives and the like in the methods disclosed and claimed herein.

In certain particularly preferred embodiments, the second antibody may contain a detectable reporter moiety or label such as an enzyme, dye, radionuclide, luminescent group, fluorescent group or biotin, or the like. The amount of the second antibody that remains bound to the solid support is then determined using a method appropriate for the specific detectable reporter moiety or label. For radioactive groups, scintillation counting or autoradiographic methods are generally appropriate. Antibody-enzyme conjugates may be prepared using a variety of coupling techniques (for review see, e.g., Scouten, W. H., *Methods in Enzymology* 135:30-65, 1987). Spectroscopic methods may be used to detect dyes (including, for example, colorimetric products of enzyme reactions), luminescent groups and fluorescent groups. Biotin may be detected using avidin or streptavidin, coupled to a different reporter group (commonly a radioactive or fluorescent group or an enzyme). Enzyme reporter groups may generally be detected by the addition of substrate (generally for a specific period of time), followed by spectroscopic, spectrophotometric or other analysis of the reaction products. Standards and standard additions may be used to determine the level of mesothelin polypeptide in a sample, using well known techniques.

In another embodiment, the invention contemplates the use of a mesothelin related antigen polypeptide as provided herein to screen for the presence of a malignant condition by detection of immunospecifically reactive antibodies in a biological sample from a biological source or subject. According to this embodiment, a mesothelin related antigen polypeptide (or a fragment or variant thereof including a truncated mesothelin related antigen polypeptide as provided herein) is detectably labeled and contacted with a biological sample to detect binding to the mesothelin related antigen polypeptide of an antibody naturally occurring in soluble form in the sample. For example, the mesothelin related antigen polypeptide may be labeled biosynthetically by using the sequences disclosed herein in concert with well known methods such as incorporation during in vitro translation of a readily detectable (e.g., radioactively labeled) amino acid, or by using other detectable reporter moieties such as those described above. Without wishing to be bound by theory, this embodiment of the invention contemplates that certain mesothelin polypeptides such as the MRA polypeptides disclosed herein, which feature frame-shifted sequences that result from in-frame insertions of coding sequences at the nucleic acid level, may provide peptides that are particularly immunogenic and so give rise to specific and detectable antibodies. For example, according to this theory certain MRA polypeptides may represent "non-self" antigens that provoke an avid immune response, while mesothelin polypeptides that lack in-frame insertions (e.g., MPF or mesothelin) may be viewed by the immune system as "self" antigens that do not readily elicit humoral or cell-mediated immunity.

As noted above, the present invention pertains in part to the surprising finding that soluble forms of human mesothelin related antigen polypeptides occur naturally in subjects, including elevated levels of such soluble mesothelin polypeptides in subjects having certain carcinomas.

A method of screening for the presence of a malignant condition according to the present invention may be further enhanced by the detection of more than one tumor associated marker in a biological sample from a subject. Accordingly, in certain embodiments the present invention provides a method of screening that, in addition to detecting reactivity of a naturally occurring soluble sample component with an antibody specific for a mesothelin related antigen polypeptide, also includes detection of at least one additional soluble marker of a malignant condition using established methods as known in the art and provided herein. As noted above, there are currently a number of soluble tumor associated antigens that are detectable in samples of readily obtained biological fluids. These include, but need not be limited to, CEA, CA125, sialyl TN, SCC, TPS and PLAP, (see e.g., Bast et al., 1983 N. Eng. J. Med. 309:883; Lloyd et al., 1997 Int. J. Canc. 71:842; Sarandakou et al., 1997 Acta Oncol. 36:755; Sarandakou et al., 1998 Eur. J. Gynaecol. Oncol. 19:73; Meier et al., 1997 Anticanc. Res. 17(4B):2945; Kudoh et al., 1999 Gynecol. Obstet. Invest. 47:52; Ind et al., 1997 Br. J. Obstet. Gynaecol. 104:1024; Bell et al. 1998 Br. J. Obstet. Gynaecol. 105:1136; Cioffi et al., 1997 Tumori 83:594; Meier et al. 1997 Anticanc. Res. 17(4B):2949; Meier et al., 1997 Anticanc. Res. 17(4B): 3019) and may further include any known marker the presence of which in a biological sample may be correlated with the presence of at least one malignant condition, as provided herein.

Alternatively, nucleic acid sequences encoding mesothelin related antigen polypeptides may be detected, using standard hybridization and/or polymerase chain reaction (PCR) techniques. Suitable probes and primers may be designed by those of ordinary skill in the art based on the mesothelin related antigen cDNA sequences provided herein. Assays may generally be performed using any of a variety of samples obtained from a biological source, such as eukaryotic cells, bacteria, viruses, extracts prepared from such organisms and fluids found within living organisms.

The following Examples are offered by way of illustration and not by way of limitation.

EXAMPLES

Example 1

Monoclonal Antibody OV569 Specific for Mesothelin Polypeptide

This example describes generation of a murine monoclonal antibody (Mab), OV569, following immunization with human malignant ascites cells from ovarian carcinoma. Cells for use as immunogens were unfractionated cells recovered from peritoneal ascites fluids of a patient with malignant ovarian cancer by centrifugation, washed and stored in liquid nitrogen until use. BALB/c mice (approximately 3 months old) were immunized a total of seven times at 14-day intervals with $1 \times 10^7$ thawed ovarian carcinoma cells per immunization; no adjuvant was used. For the initial immunization, mice were injected both intraperitoneally (i.p.) and subcutaneously (s.c.), while for the remaining six immunizations, injections of thawed cells were administered only i.p. Four days after the last immunization, the spleen was removed from one mouse, teased apart to form a single cell suspension in IMDM culture medium (Gibco BRL, Grand Island, N.Y.) and the splenocytes subsequently fused to myeloma cells P3x63Ag8.653 (CRL 1580, ATCC, Rockville, Md.) as previously described using 40% polyethylene glycol (PEG) as the fusing agent (Yeh et al., 1979 Proc. Nat. Acad. Sci. USA 76:2927). Following hybridization, the fused cell suspensions were diluted to form low density cultures preferably originating from single cells, and seeded into 96 well plates (Falcon, Linden Park, N.Y.) in selective medium containing 10% hybridoma growth factor (Igen Inc, Gaithersburg, Mo.), 10% fetal bovine serum, 2% HAT and 0.25% Geneticin (Yeh et al., 1979).

Supernatants from each well were screened for the presence of antibodies capable of binding to the ovarian carcinoma ascites cells used for immunizations, to cultured ovarian carcinoma cells from other patients, and to cultured human fibroblasts, using an enzyme linked immunosorbent assay (ELISA) as described by Douillard, et al. (1983 Meth. Enzymol. 92:168). Hybridoma cells that produced antibodies that bound to the human ovarian cancer cells but not to the cultured human fibroblasts were cloned twice by limiting dilution, re-tested for specific reactivity of supernatant antibody with the ovarian cancer cells (and for non-reactivity with cells from a variety of normal human tissues) and expanded in vitro. Antibodies were purified from hybridoma supernatants by affinity chromatography on immobilized protein A (RepliGen, Cambridge, Mass.), using phosphate buffered saline (PBS) as buffer and low pH elution followed by neutralization as recommended by the supplier, after which they were filter sterilized and stored at −70° C. until use.

One such monoclonal hybridoma antibody that bound ovarian carcinoma cells but not normal fibroblasts was named OV569. Monoclonal antibody (MAb) OV569 was determined to be of the murine IgG1 isotype by ELISA. Briefly, wells of an Immunolon 96 well plate (Dynatech, Chantilly, Va.) were coated overnight at 4° C. with goat antibodies (1 μg/ml in PBS) specific for the different mouse IgG subclasses (Southern Biotech, Birmingham, Ala.), blocked and used to test various dilutions of OV569 hybridoma supernatant according to a described procedure (Yeh et al., 1979 *Proc. Nat. Acad. Sci. USA* 76:2927).

Example 2

Second Generation Monoclonal Antibodies Specific for Ovarian Carcinoma Antigen Recognized by OV569

A second set of hybridomas was generated and selected for production of antibodies that bind to the antigen molecule recognized by MAb OV569, but via recognition of antigenic epitopes distinct from that used by OV569. For use as an immunogen to elicit the second generation MAbs, the OV569-binding antigen was affinity purified from supernatants of human ovarian and lung carcinoma cell cultures established from surgically removed tumors (as described, for example, by Hellstrom et al., 1990 *Cancer Res.* 50:2183) or following collection of ascites or pleural fluids using a column of immobilized MAb OV569. Briefly, to 1.5 g cyanogen bromide activated Sepharose 4B (Sigma, St. Louis, Mo.) 9.2 mg of OV569 was added and the column washed and equilibrated for use according to the supplier's protocol. Starting material from which antigen was to be purified (e.g., culture supernatant clarified by centrifugation) was passed through the column, after which the column was washed with 0.01 M 0.02% $NaN_3$ in PBS-pH 7.2, until no material having absorbance at 280 run was detectable in the column effluent. Soluble antigen specifically bound to the MAb OV569 column was then eluted using a pH 2.6 elution buffer (0.1 M glycine-HCl-pH 2.6, 0.15 M NaCl). The eluate was collected in a volume of 2 ml, neutralized with 2.5 M Tris-HCl buffer, pH 8.8, and quantified by spectrophotometric determination of absorbance at 280 nm and 260 run.

Affinity purified OV569 antigen (30 µg protein in 0.1 ml) was mixed with 0.1 ml of Ribi adjuvant (Ribi Immunochem. Research, Inc., Hamilton, Mont.) and the mixture was injected into 3 month old BALB/c mice at two s.c. sites, followed 14 days later by a first booster immunization, which was administered i.p. For booster immunizations, the Ribi adjuvant was mixed with antigen purified by OV569 affinity chromatography from the supernatant of cultured H4013 lung carcinoma cells (a carcinoma cell line established using the methods as described, for example, by Hellstrom et al., 1990 *Cancer Res.* 50:2183). Fourteen days after administration of the third in a series of three booster immunizations (each given at 14 day intervals), the mice were given a final boost by injecting the antigen intravenously (i.v without adjuvant.

Three days after the final boost, spleens were removed and cell fusions were performed as described above in Example 1 for MAb OV569. The supernatants of the resultant hybridoma cells were tested for the presence of antibodies capable of binding to target antigen immobilized on plastic 96 well plates using conventional ELISA methods (*Current Protocols in Immunology*, J. E. Coligan et al., (Eds.) 1998 John Wiley & Sons, NY). Target antigen was (i) affinity purified OV569 antigen (the immunizing antigen) prepared as described above; or (ii) D2hIg, an immunoglobulin fusion protein consisting of amino acids 294-628 of the mesothelin membrane-bound portion (SEQ ID NO: 19) (Chang et al., 1996 *Proc. Nat. Acad. Sci.* USA 93:136) fused to an immunoglobulin constant region using a described vector encoding a human Ig sequence (Hollenbaugh et al., 1995 *J. Immunol. Meth.* 188:1-7) and purified by protein A/G affinity chromatography (ImmunoPure A/G, Pierce Chemicals, Rockford, Ill.) according to the supplier's instructions.

Positive supernatants were re-tested by ELISA to confirm reactivity and subsequently screened in a modified ELISA binding competition immunoassay. Briefly, in this assay, OV569-binding antigen, affinity purified as described above, was immobilized in wells of 96 well plates. Wells received of each positive hybridoma supernatant and 50 µl (400 ng) of biotinylated MAb OV569 prepared by biotinylation according to Weir, D. M., *Handbook of Experimental Immunology* (1986, Blackwell Scientific, Boston), for a binding competition incubation step (1 hr at room temperature) followed by washing with PBS and a detection step using 50 µl HRP-streptavidin (PharMingen, San Diego, Calif.) diluted according to the supplier's recommendations. This assay selected for MAbs that recognized epitopes different from the one recognized by OV569, by virtue of their inability to inhibit biotinyl-MAb OV569 binding. Supernatants tested in this competition assay were also tested using a parallel set of control plates coated with the affinity purified OV569 binding antigen to confirm hybridoma antibody binding to the OV569 antigen. Three hybridomas, designated 4H3, 3G3 and 1A6, were identified that produced antibodies capable of binding to D2hIg and to OV569 affinity-purified antigen from cultured OV569-positive carcinoma culture supernatants, and that did not compete with the OV569 MAb. These three hybridomas were cloned, expanded and transplanted in syngeneic mice to establish antibody-producing ascites tumors. The IgG1 MAb referred to as 4H3 was used with OV569 in a double determinant ("sandwich ELISA") assay described below.

Example 3

Expression of OV569 Ovarian Carcinoma Antigen on Human Tumor Cell Surfaces

This example describes immunohistologic characterization of the expression of the antigen defined by MAb OV569. A modification of the immunoperoxidase technique (Sternberger, In: Immunocytochemistry, pp. 104-169, John Wiley & Sons, Inc., New York, 1979) was employed, using the Vectastain ABC immunostaining reagent system (Vector Laboratories, Burlingame, Calif.) according to the manufacturer's instructions. Briefly, various normal human tissues or human tumor samples were obtained by standard surgical resection or biopsy procedures and immediately frozen. The frozen samples were sectioned using a chilled microtome, air-dried on glass microscope slides, fixed with cold acetone (5 min, −20° C.), washed twice in PBS, blocked with normal mouse serum (20 min, room temperature), and then treated with avidin/biotin blocking reagents. The slides were next incubated with primary antibodies diluted in Vectastain blocking solution (Vector Laboratories) for 90 min at room temperature and washed with PBS. Slides were then incubated with biotinylated goat anti-mouse IgG (Southern Biotechnology Assoc., Birmingham, Ala.) diluted 1:150 in Vectastain blocking solution for 30 min at room temperature, and again washed with PBS. A Vectastain ABC ("Vector Elite") horseradish peroxidase (HRP) working solution was prepared and kept at room temperature. The slides were incubated with this HRP solution for 30 min at room temperature, washed 3 times with PBS, and rinsed in Tris buffer (0.05M Tris-HCl-pH 7.5, 150 mM NaCl). A diaminobenzamidine (DAB, Bio-Tek Instruments, Inc., Winooski, Vt.) chromogen reagent solution was prepared daily according to the Vectastain ABC instructions, and the slides were incubated with this reagent for 7 min. at room temperature in subdued light. The reaction was stopped by adding PBS and washing twice with double distilled water. Slides were counterstained with hematoxylin (Bio-Tek Hematoxylin solution diluted 1:10 with distilled water) for 10-45 seconds, rinsed three times with water and dehydrated through a graded ethanol series prior to mounting for microscopy.

The slides were coded and examined by an independent investigator, who photographed representative microscope fields using differential interference contrast (Nomarski) optics under bright-field illumination with a Zeiss upright microscope (Carl Zeiss, Inc., Thornwood, N.Y.). As presented here, samples were scored as "positive" when at least one third of the cells examined showed DAB staining; samples referred to as "negative" exhibited no significant staining (<5% of cells) using the same MAb dilutions. Table 1 shows the ratio of positively staining cancer ("Ca.") specimens relative to the number of cancer specimens tested. The staining was seen in the cytoplasm of the tumor cells and, in some cases, also at the cell surface. No staining of normal (i.e., non-cancerous) cells was observed with MAb OV569. Both neoplastic cells and stromal cells were observed in tumor samples, and only the former were stained by MAb OV569. Results using normal human tissue samples are shown in Table 2.

TABLE 1

IMMUNOHISTOLOGICAL STAINING OF HUMAN TUMORS WITH MAB OV569

| Tumors | Positive/Tested |
|---|---|
| Ca. ovary | 20/21 |
| Ca. endometrium | 3/7 |
| Ca. cervix uteri | 5/8 |
| Ca. breast | 4/18 |
| Ca. stomach | 3/7 |
| Ca. colon | 2/15 |
| Ca. testis | 0/2 |
| Ca. lung (non-small cell) | 5/13 |
| Ca. lung (small cell) | 0/3 |
| Ca. bladder | 0/6 |
| Ca. prostate | 0/14 |
| Melanoma | 0/8 |

TABLE 2

IMMUNOHISTOLOGICAL STAINING OF NORMAL HUMAN TISSUES WITH MAB OV569*

| Normal Tissue | Positive/Tested |
|---|---|
| adrenal | 0/6 |
| brain | 0/7 |
| breast | 0/7 |
| cecum | 0/3 |
| colon | 0/6 |
| endometrium | 1/6 |
| esophagus | 0/5 |
| heart | 0/8 |
| ileum* | 5/5* |
| jejunum | 0/4 |
| kidney | 0/7 |
| liver | 0/8 |
| lung | 0/6 |
| lymph node | 0/1 |
| mesothelium | 1/1 |
| nerve | 0/6 |
| ovary | 0/6 |
| pancreas | 0/6 |
| placenta | 0/2 |
| prostate | 0/7 |
| benign prostatic hypertrophia | 0/5 |
| skin | 0/6 |
| stomach | 0/6 |
| spleen | 0/8 |
| thyroid | 0/4 |
| testis | 0/12 |
| tonsil | 0/4 |

*Weak staining of a subpopulation (<10%) of cells

Example 4

Expression of OV569 Ovarian Carcinoma Antigen on Cultured Human Carcinoma Cell Surfaces In this example, MAb OV569 binding to carcinoma cell surface antigens was evaluated by flow immunocytofluorimetry using a Coulter Epics C FACS cytofluorimeter (Coulter Corp., Miami, Fla.) essentially as previously described (Hellstrom et al., 1986 *Canc. Res.* 46:3917). Cultured adherent human carcinoma cells generated as described above (e.g., Hellstrom et al., 1990 *Cancer Res.* 50:2183) were removed from culture flasks with trypsin/EDTA, washed two times by centrifugation (200×g, 10 min) and resuspension in IMDM medium (GibcoBRL, Grand Island, N.Y.) containing 15% FBS and equilibrated for at least 1 h at room temperature in the same medium. Aliquots of the cells ($0.5$-$1.0 \times 10^6$ cells/0.1 ml for each group) were then held on ice for 15 min and resuspended for 1 h at 4° C. in 100 µl OV569 hybridoma cell culture supernatant. The cells were washed three times in staining buffer (IMDM medium containing 5% fetal calf serum) and resuspended for 30 min. at 4° C. in 0.1 mL per group of fluorescein-conjugated goat anti-mouse immunoglobulin (FITC-GaMIg, BioSource International, Inc., Camarillo, Calif.) diluted in staining buffer according to the supplier's recommendations. Cells were again washed three times, resuspended in 0.5 mL chilled staining buffer and maintained at 4° C. in the dark until analysis. Flow immunocytofluorimetry was performed using the Coulter Epics C FACS cytofluorimeter (Coulter Corp., Miami, Fl.) according to the manufacturer's instructions, with forward and side-scatter parameters gated to record single-cell events. The mean fluorescence intensity was determined for each sample and used to calculate the linear fluorescence equivalence (LFE) using the software with which the Coulter Epics C FACS was equipped. The LFE of each test sample divided by the LFE of a negative control sample (incubated with a MAb of irrelevant specificity during the first antibody incubation step) provided a ratio for comparing the relative brightness of specifically immunofluorescently stained cells to that of cells stained with the negative control antibody. The results are shown in Table 3.

TABLE 3

FLOW IMMUNOCYTOFLUORIMETRIC ANALYSIS OF OV569 EXPRESSION BY CULTURED HUMAN CARCINOMA CELLS

| CARCINOMA TYPE | CELL LINE | LFE(sample)/ LFE(control) |
|---|---|---|
| Ovarian | H3538 | 2.55 |
| Ovarian | H3907 | 3.85 |
| Ovarian | H3909 | 3.84 |

TABLE 3-continued

FLOW IMMUNOCYTOFLUORIMETRIC ANALYSIS OF OV569 EXPRESSION BY CULTURED HUMAN CARCINOMA CELLS

| CARCINOMA TYPE | CELL LINE | LFE(sample)/LFE(control) |
|---|---|---|
| Ovarian | H4004 | 2.43 |
| Ovarian | H3633 | 1.0 |
| Ovarian | H3750 | 2.57 |
| Ovarian | H3759 | 6.74 |
| Ovarian | H3659.5 | 5.63 |
| Ovarian | H4002 | 8.48 |
| Ovarian | H4014 | 1.0 |
| Ovarian | H4006 | 2.53 |
| Ovarian | H4007 | 8.72 |
| Ovarian | H4010-1 | 1.12 |
| Ovarian | H4012 | 1.0 |
| Lung | H4013 | 7.0 |
| Lung | H2981 | 1.3 |
| Lung | H2987 | 1.25 |
| Lung | H3963 | 1.11 |
| Lung | H3776 | 1.33 |
| Lung | H3754 | 1.59 |

Example 5

Human Carcinoma Cells Fail to Internalize OV569 Ovarian Carcinoma Antigen

To determine whether the antigen defined by MAb OV569 can be internalized by antigen positive carcinoma cells, immunofluorescence antibody localization assays were performed using laser scanning confocal microscopy. Human lung carcinoma cells (H4013), or ovarian carcinoma cells (H4007) adapted to culture following surgical resection as described above (e.g., Hellstrom et al., 1990 Cancer Res. 50:2183) were cultured in IMDM culture medium (Gibco BRL, Grand Island, N.Y.) containing 10% fetal calf serum and allowed to adhere onto glass slides (NUNC chamber coverslips, NUNC, Rochester, N.Y.) for 48 hrs at 37° C., 5% $CO_2$ in a humidified atmosphere. For immunofluorescent antibody labeling, the cells were equilibrated for 15 min at 4° C., a temperature that is non-permissive for internalization of cell surface antigens. FITC-conjugated OV569 was prepared by incubation of fluorescein isothiocyanate (Sigma, St. Louis, Mo.) under described conditions (Weir, D. M., Handbook of Experimental Immunology, 1986, Blackwell Scientific, Boston) with MAb OV569 affinity purified on immobilized protein A (RepliGen, Cambridge, Mass.) according to the manufacturer's recommendations. Either FITC-OV569, or, as a negative control, FITC conjugated goat anti-mouse IgG (Tago, Burlingame, Calif.), was added to the cells at a concentration of 10 µg/ml for 1 hr. at 4° C., in a volume sufficient to cover each coverslip. Unbound antibody was removed by extensively rinsing the coverslips with cold culture medium. The cells were then incubated for different periods of time at 37° C., a temperature that is permissive for internalization of certain cell surface antigens (Hellstrom et al., 1990 Canc. Res. 50:2183). The 37° C. incubation period was terminated by adding cold PBS to the cultures and post-fixing the cells with 2% formaldehyde in PBS for 15 min. at room temperature. Each coverslip was then treated with the anti-fading reagent dithioerythritol (Sigma, St. Louis, Mo.) or with the VectaStain anti-fading reagent (Vector Laboratories, Burlingame, Calif.) according to the supplier's instructions. Laser scanning confocal microscope images were obtained using a Leica confocal microscope (Leica, Inc., Deerfield, Ill.) equipped with a fluorescein detection filter set according to the manufacturer's instructions.

Confocal images demonstrated exclusive localization of FITC-MAb OV569 to the surfaces of human ovarian carcinoma and lung carcinoma cells exposed to the antibody at 4° C., washed and immediately fixed. When cells stained with FITC-MAb OV569 at 4° C. were shifted to 37° C. for periods of 8 h or longer, detectable FITC-MAb OV569 remained exclusively localized to cell surfaces and no cytoplasmic fluorescent staining was observed.

Example 6

Immunoblot Characterization of OV569 Ovarian Carcinoma Antigen

This example describes characterization of the human carcinoma cell surface antigen recognized by MAb OV569 using Western immunoblot analysis.

Samples for immunoblot analysis included lysates were prepared from the following human cell lines: H4013 lung carcinoma (FIG. 1, lane 5), OVCAR-3 ovarian carcinoma (Amer. Type Culture Collection, Manassas, Va.) (FIG. 1, lane 7), and 6K kidney carcinoma (FIG. 1, lane 8) cell lysates were prepared according to standard procedures (Current Protocols in Immunology, J. E. Coligan et al., (Eds.) 1998 John Wiley & Sons, NY). Protein was quantified using the Bradford Commassie protein assay reagent (Pierce Chemicals, Inc., Rockford, Ill.) according to the manufacturer's instructions.

Other samples for immunoblot analysis included material derived from human patients and affinity purified on a column of immobilized MAb OV569 as described above in Example 2. These samples included OV569 affinity-purified fractions of ovarian cancer ascites fluid from a patient having ovarian carcinoma (FIG. 1, lane 2), and of pleural effusion fluid collected from the fluid-filled interpleural membrane cavity of a patient diagnosed as having lung carcinoma (FIG. 1, lane 3). Fluid sample preparation and affinity chromatography, respectively, were as described below in Example 7 and above in Example 2.

Other samples for immunoblot analysis included material derived from human carcinoma cell lines and affinity purified on a column of immobilized MAb OV569 as described above in Example 2. These samples included OV569 affinity-purified fractions of H4013 lung carcinoma (FIG. 1, lane 4), OVCAR-3 ovarian carcinoma (ATCC, Manassas, Va.) (FIG. 1, lane 6). The D2hIg fusion protein described in Example 2 was also analyzed (FIG. 1, lane 1).

Each sample standardized by protein content was diluted 1:1 with SDS sample buffer (Novex, San Diego, Calif.), 20 µl (300 ng/lane) was loaded onto a 14% Tris-glycine gel (Novex, San Diego, Calif.) and the gel was subject to electrophoresis using SDS running buffer at 125 V for about 1.5 hours according to the manufacturer's instructions. Following gel electrophoresis, separated proteins were electroblotted onto PVDF membrane (Novex, San Diego, Calif.) using Tris-glycine SDS transfer buffer and electrophoretic transfer conditions as recommended by the manufacturer.

Prior to antibody probing, the PVDF membrane was blocked with 5% nonfat milk in washing buffer (0.2% Tween 20-PBS) at room temperature for 1 hr, followed by washing with washing buffer, once for 10 minutes and twice for 5 minutes. Next, the membrane was bathed in a solution of protein A affinity purified MAb OV569 (4.6 mg/ml) diluted to 3 µg/mL in washing buffer containing 1% nonfat milk at room temperature for 1 hour, followed by a sequence of 3 washes as described above. Detection of specifically bound MAb OV569 was achieved using chemiluminescent detection of horseradish peroxidase (HRP) conjugated secondary antibodies. Briefly, the membrane was incubated for 1 hr at room temperature in a 1:5000 dilution of HRP-labeled goat anti-mouse IgG antibody (Zymed Laboratories, South San Francisco, Calif.) in washing buffer containing 1% nonfat milk, and then unbound antibodies were removed by bathing the blot in washing buffer once for 10 minutes, and then 4 times for 5 minutes each. The ECL chemoluminescence substrate (ECL-Amersham, Buckinghamshire, England) was applied onto the membrane for 1 minute in a dark room according to the supplier's instructions, followed by brief exposure to X-omat radiology film (Kodak, Rochester, N.Y.).

FIG. 1 shows the pattern of electrophoretically resolved species that were detected by binding MAb OV569, which identifies a component having an apparent relative molecular mass of 42-45 kDa in samples derived from various human carcinomas.

Example 7

Mesothelin Related Antigen (MRA), a Carcinoma Antigen Recognized by Monoclonal Antibody OV569 is a Mesothelin Polypeptide This example describes identification of a molecule that naturally occurs in soluble form in a biological sample from a carcinoma patient, and that is recognized by MAb OV569, as a mesothelin polypeptide. This naturally soluble mesothelin polypeptide is referred to herein as "mesothelin related antigen" (MRA).

Pleural effusion fluid (2 liters) collected into heparinized tubes by a single drawing from a patient diagnosed as having lung carcinoma was clarified by centrifugation to remove cells, diluted 1:1 (v/v) with PBS and filtered through 3 MM filter paper (Whatman, Clifton, N.J.) prior to immunoaffinity chromatography. The diluted pleural fluid was applied to a column of immobilized MAb OV569, the column was washed to remove non-binding components and specifically bound material was eluted and collected as described in Example 2. Bound and eluted fractions were neutralized by addition of 3 mM glycine-0.2 N NaOH neutralization buffer. The pooled, eluted OV569-binding material was alkylated by addition of several grains of crystalline iodoacetamide (Sigma, St. Louis, Mo.) to block artifactual disulfide bond formation through potentially present cysteine residues, and the material was resolved by SDS-polyacrylamide gel electrophoresis and blot transferred to a PVDF membrane as described in Example 6, except that the resolving gel contained 7.5% polyacrylamide. A lane of the PVDF membrane was immunostained with MAb OV569 as also described in Example 6 to localize a diffuse band of approximately 40 kDa for N-terminal sequence analysis.

The amino acid sequence of the approximately 40 kDa band was analyzed by sequential Edman degradation on an ABI Model 473 solid-phase sequencer (Applied Biosystems Inc., Foster City, Calif.). Partial sequence analysis revealed the following N-terminal amino acid sequence for the OV569 affinity-isolated 40 kDa polypeptide:

EVEKTACPSGKKAREIDES SEQ ID NO:5 SEQ ID NO:5

This amino acid sequence represents a partial amino acid sequence of a novel, naturally soluble member of the mesothelin polypeptide family. Because the amino acid sequence of SEQ ID NO:5 is also present at positions 294-312 of mesothelin (SEQ ID NO: 20), a cell surface differentiation antigen expressed on mesothelium, mesotheliomas and ovarian cancers that is not detectable as a naturally soluble molecule as provided herein (Chang et al., 1992 *Int. J. Canc.* 50:373; Chang et al., 1996 *Proc. Nat. Acad. Sci. USA* 93:136), the soluble OV569-binding polypeptide described here has been termed "mesothelin related antigen" (MRA). As noted above, the amino acid sequence of SEQ ID NO:5 is also present in the cell surface membrane-bound (i.e., not soluble as provided herein) portion of the MPF precursor protein (SEQ ID NO: 21) (Kojima et al., 1995 *J. Bid. Chem.* 270:2 1984).

Figure 2:
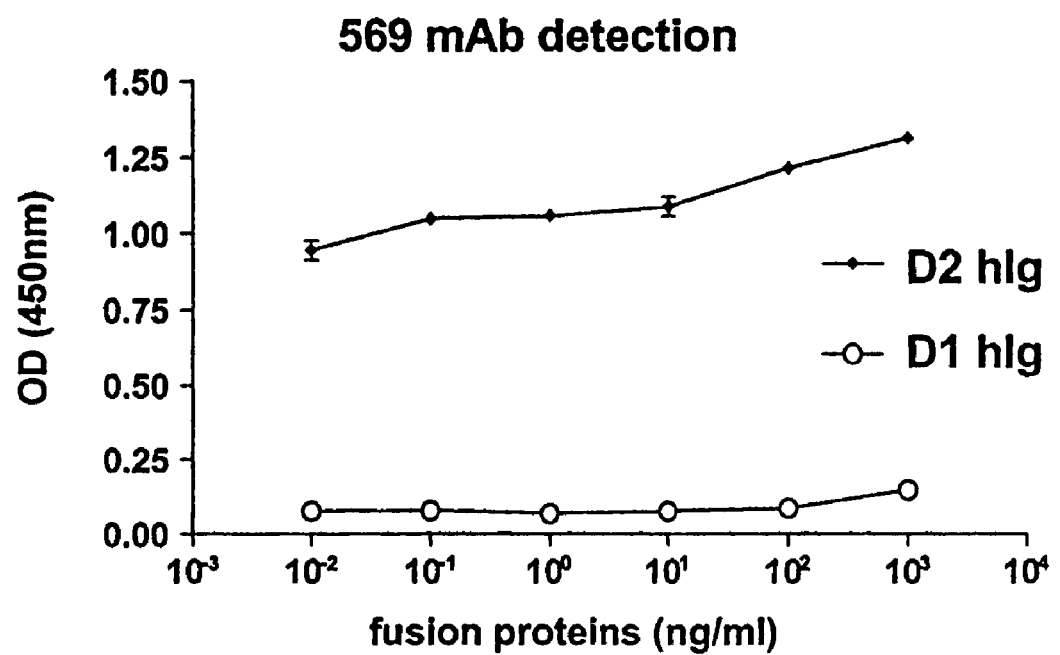
FIG. 2 shows monoclonal antibody OV569 binding to human immunoglobulin constant region fusion proteins containing soluble (D1hIg) or membrane-associated (D2hIg) domains of MPF in ELISA.

As noted above, mesothelin and MPF are synthesized as approximately 70 kDa precursors that are proteolytically processed into soluble and cell surface-bound products (Chang et al., 1996 *Proc. Nat. Acad. Sci. USA* 93:136; Chowdhury et al., 1998 *Proc. Nat. Acad. Sci. USA* 95:669; Kojima et al., 1995 *J. Biol. Chem.* 270:21984; Yamaguchi et al., 1994 *J. Biol. Chem.* 269:805). To identify the domain (soluble or membrane associated) in which the OV569 epitope resided, two human immunoglobulin constant region fusion proteins were constructed. D1hIg contained the 33 kDa MPF soluble domain (Chang et al., 1996; Kojima et al., 1995), while D2hIg contained the 44 kDa membrane-bound domain of MPF (Chang et al., 1996; see Example 2). OV569 specificity was tested by conventional ELISA methods as described above. As shown in FIG. 2, OV569 bound to D2hIg but failed to recognize D1hIg.

Example 8

Assay for Detection of Ovarian Carcinoma Antigen Defined by Monoclonal Antibody OV569 in Malignant Effusion and Sera of Patients This example describes a sandwich ELISA immunoassay for the detection of MRA, a novel, naturally soluble member of the mesothelin polypeptide family. The assay employs MAb OV569 and MAb 4H3, which bind to distinct epitopes present on MRA.

The wells of Maxisorp Immuno™ plates (Nalge Nunc International, Napeville, Ill.) plates were coated overnight at 4° C. with 50 ng of protein A immunoaffinity (ImmunoPure A/G IgG Purification Kit, Pierce Chemicals, Rockford, Ill.) purified MAb 4H3 immunoglobulin in 50 µl/well of carbonate-bicarbonate buffer (C-3041, Sigma). The next day, wells were drained and blocked for 2 h at room temperature with 200 µl/well of GSC blocking buffer (Genetic Systems Corp., Redmond, Wash.). Wells were then washed four times with 200 µl/well of PBS containing 0.1% Tween 20 (Fischer Chemicals, Fairlawn, N.J.).

To initiate the assay, 100 µl per well of serial doubling dilutions (1:40 to 1:1280) of patient sera diluted in blocking buffer were added, and plates held at room temperature for 1 h. Wells were washed four times with PBS-0.1% Tween-20, after which 50 µl/well of biotinylated MAb OV569 (prepared as described in Example 2), 200 ng/ml in conjugate diluent (Genetic Systems) was added and allowed to incubate for 1 h at room temperature. Wells were again washed four times with PBS-Tween. Next, 50 µl/well HRP-streptavidin (PharMingen, San Diego, Calif.) diluted 1:1000 in conjugate diluent was added and the plates held at room temperature for 45 min. Wells were washed four times with PBS-Tween and developed by adding buffered 3,3',5,5'-tetramethylbenzidine (TMB, Genetic Systems) plus 1% (v/v) of the HRP-streptavidin conjugate for 15 min. The reaction was stopped by addition of 2M $H_2SO_4$, and the plates were read at 460 nm using a Spectracount microplate spectrophotometer (Packard Instrument Co., Meriden, Conn.).

Positive and negative control serum samples from two patients were included in all assays. The negative control serum came from a healthy volunteer and gave no detectable signal when present at a 1:40 dilution. The positive control ("c+") came from a patient diagnosed with ovarian carcinoma and provided a readily detectable signal under the described assay conditions when present at a 1:1280 dilution or less.

Figure 3:
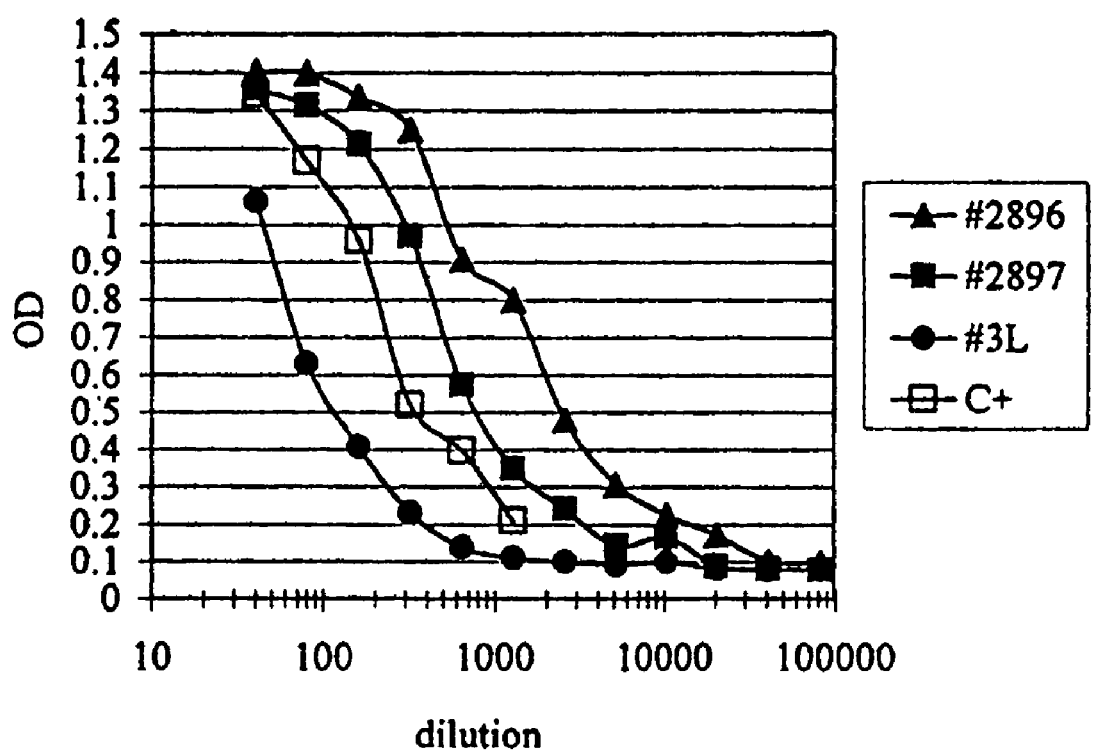
FIG. 3 depicts detection of soluble mesothelin polypeptides in sera from carcinoma patients by sandwich ELISA.

FIG. 3 illustrates representative results using the sandwich ELISA immunoassay for the detection of MRA. Soluble molecules recognized by the two MAbs, 4H3 and OV569, were readily detected in sera from two ovarian carcinoma patients (#2896 and #2897) and in serum from a lung carcinoma patient (#3L), and could be relatively quantified as titratable reactivities. The positive control serum (c+) also exhibited reactivity with the MRA-binding MAbs, which decreased as the dilution factor increased.

Figure 4:
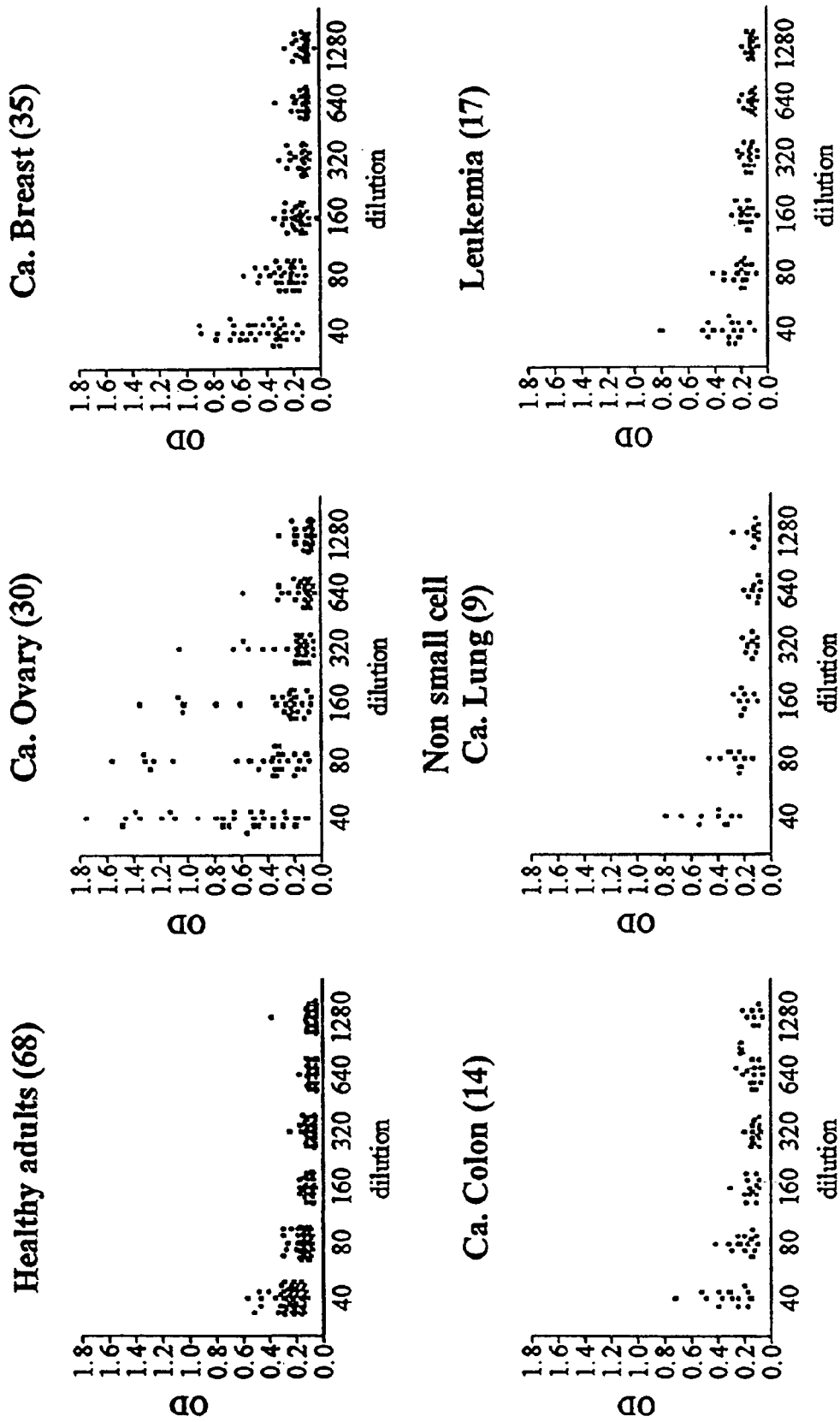
FIG. 4 illustrates detection using sandwich ELISA of soluble mesothelin polypeptides in sera from normal subjects and from patients diagnosed with malignant conditions.

Sera from additional patients diagnosed as having ovarian carcinoma, and also from patients with various other tumors were assayed using the sandwich ELISA immunoassay for the detection of MRA. Additional patient sera having non-neoplastic diseases and sera from healthy patients were also compared using this assay. A summary of the results is graphically depicted in FIG. 4. At a serum dilution of 1:160, 23 of 30 sera from patients who had ovarian carcinoma in stage 3 or stage 4 exhibited circulating MRA levels that were significantly elevated, compared to 0 of 68 sera from healthy volunteers. Using the same criteria, 25 of 75 sera from patients with tumors other than ovarian carcinoma exhibited detectable reactivity in the MRA sandwich ELISA, with the highest frequency of positive sera (66%) being observed in patients with lung carcinoma (Table 4). Sera from three patients with non-neoplastic diseases were negative in the MRA sandwich ELISA.

TABLE 4

| Diagnosis | Number of sera with OD > 3SD above negative | Number of sera tested |
| --- | --- | --- |
| control sera | 0 | 68 |
| Ca. Ovary | 23 | 30 |
| Ca. Breast | 11 | 35 |
| Ca. Lung | 6 | 9 |
| Ca. Colon | 2 | 14 |
| Leukemias | 6 | 17 |

Example 9

Molecular Cloning and Sequencing of Nucleic Acid Sequence Encoding a Mesothelin Related Antigen (MRA-1)

Because monoclonal antibody OV569 recognized the membrane bound (D2hIg) but not the soluble (D1hIg) domain of MPF, but also could be used to affinity isolate a soluble polypeptide from pleural effusion fluid (Example 7), the identity of a novel mesothelin related antigen (MRA) was determined. This example describes the cloning and sequencing of a cDNA molecule encoding an MRA, MRA-1 (SEQ ID NO: 3'), from a human prostatic carcinoma cell line, using sequence information from the antigen defined by monoclonal antibody OV569. Plasmid isolation, production of competent cells, transformation and M13 manipulations were carried out according to published procedures (Sambrook et al., *Molecular Cloning, a Laboratory Manual*, Cold Spring Harbor Laboratory Press, Cold Spring Harbor, N.Y., 1989). Total RNA was isolated from a human prostatic carcinoma cell line (HE1P generated as described above, see. e.g., Hellstrom et al., 1990 *Cancer Res.* 50:2183) using an RNAgents™ kit (Promega, Inc., Madison, Wis.) and polyA+ RNA was purified from the total RNA with an mRNA Separator™ (Clontech, Inc., Palo Alto, Calif.), both according to the manufacturer's recommendations. A Marathon™ cDNA amplification kit (Clontech, Palo Alto, Calif.) was used to reverse transcribe the RNA and make double-stranded cDNA, which was ligated to an adaptor provided with the Marathon™ kit and amplified using the EXPAND™ high fidelity PCR system (Roche Molecular Biochemicals, Indianapolis, Ind.) according to the supplier's instructions. For this amplification, the first oligonucleotide primer was specific for the Marathon™ adaptor sequence and the second primer corresponded to the coding region for the N-terminal sequence of the OV569 antigen [SEQ ID NO:5] and had the following sequence derived from the MPF cDNA sequence (Kojima et al., 1995):

GSP1: 5'-GGA AGT GGA GAA GAG AGC CTG TCC TTC-3' SEQ ID NO:6

The PCR product was ligated into pGEM-T vector (Promega, Madison, Wis.) and the ligation mixture was transformed into DH5α competent cells (Life Technologies, Gathersburg, Md.), both according to the manufacturers' instructions. Plasmids were isolated from individual colonies of transformed DH5α cells using a QIAprep™ spin miniprep kit (Qiagen, Valencia, Calif.) and sequenced using a BigDye™ terminator cycle sequencing kit (PE Applied Biosystems, Foster City, Calif.). Ten clones were isolated, including eight that possessed a nucleic acid sequence identical to the MPF cDNA sequence (Kojima et al., 1995), one that had a sequence identical to mesothelin (Chang et al., 1996), and one that upon sequencing revealed a nucleic acid sequence (FIGS. 5A-B and SEQ ID NO:3) related to MPF and mesothelin sequences but also containing an 82 bp insert at a nucleotide position corresponding to nucleotide 1874 of the MPF coding sequence (SEQ ID NO: 22) (Kojima et al., 1995), which induced a frame shift of 212 bp.

Sequence analysis indicated that this frame shift resulted in a coding sequence for a new polypeptide referred to herein as mesothelin related antigen-1 (MRA-1) which, unlike both MPF and mesothelin, contains a hydrophilic C-terminal tail and is therefore likely to be soluble in aqueous physiological environments. The C-terminal 98 amino acids of MRA-1 were distinct from any amino acid sequences found in the C-terminal regions of either MPF or mesothelin. Surprisingly, this novel protein-encoding nucleic acid sequence (SEQ ID NO:3) included no stop codon, but instead continued directly to the polyadenylation site for the polyA tail. This lack of a stop codon may be related to the origin of this sequence in neoplastic cells. The MRA-1 sequence was more closely related to MPF than to mesothelin in that it lacked a 24 bp insertion that was present in the mesothelin DNA sequence but not the MPF sequence, and in that it was identical to MPF at two nucleotide positions where single base differences were found between MPF and mesothelin. The MRA-1 polypeptide sequence (SEQ ID NO:1) is shown in FIGS. 5A-B.

Example 10

Inverse PCR Cloning of a Mesothelin Related Antigen (MRA-2)

This example describes the cloning and sequencing of a cDNA molecule encoding an MRA variant, MRA-2 (SEQ ID NO: 4), from a human colon carcinoma cell line. MRA-2 (SEQ ID NO: 2) differs from MRA-1 (SEQ ID NO: 1) by the presence of three additional amino acids (FRR) at the N-terminus (SEQ ID NO:2) and, by virtue of the manner in which it was identified as described below, lacks the complete C-terminal region of MRA-1 (SEQ ID NO: 1'), instead terminating at the amino acid position corresponding to residue 325 of MRA-1 (SEQ ID NO: 1). Plasmid isolation, production of competent cells, transformation and related manipulations were carried out according to published procedures (Sambrook et al., *Molecular Cloning, a Laboratory Manual*, Cold Spring Harbor Laboratory Press, Cold Spring Harbor, N.Y., 1989).

Inverse PCR (Zeiner et al., 1994 *Biotechniques* 17:1051) was used to clone a nucleic acid molecule encoding a MRA from 3719 colon carcinoma, a cell line generated as described above (see, e.g., Hellstrom et al., 1990 *Cancer Res.* 50:2183). Briefly, total RNA (5 mg) was extracted from bulk cultures of 3719 cells using Trizol™ reagent (GIBCO-BRL, Grand Island, N.Y.) and polyA$^+$ mRNA was purified using PolyATtract™ oligo-dT-coated magnetic beads (Promega, Inc., Madison, Wis.) as instructed by the supplier. First strand cDNA synthesis was initiated by reverse transcription using an oligonucleotide primer specific for a portion comprising nucleotides at positions 56-80 of the 82 bp insert identified in the MRA nucleotide sequence in Example 9:

op56-80: 5'-GCG CTC TGA GTC ACC CCT CTC TCTG-3'
SEQ ID NO:7

The cDNA second strand was generated using the Marathon™ adaptor primer as described in Example 9 (Clontech, Palo Alto, Calif.). The cDNA was permitted to circularize by religating to itself for 24 hours at 15° C. using the Marathon™ kit protocol (Clontech) in a reaction volume of 200 μl. From this ligation mixture, an aliquot of 5 μl was used as template in a PCR reaction with the following primers:

```
mpf f735:   AGA AAC TTC TGG GAC CCC AC   SEQ ID NO:8
mpf r290:   GGG ACG TCA CAT TCC ACT TG   SEQ ID NO:9
``` and the following nested primers:

```
GSP-2  5'-GAA GGA CAG GCT GTC TTC TCC ACT TCC C-3'   SEQ ID NO:10
r80-54 5'-CAG AGA GAG GGG TGA CTC AGA GC-3'          SEQ ID NO:11
```

The PCR product was sequenced using a BigDye™ terminator cycle sequencing kit (PE Applied Biosystems, Foster City, Calif.). The resulting DNA sequence (SEQ ID NO:4, FIGS. 6A-B) was identical to nucleotides at positions 1-978 of the MRA-1 DNA sequence (SEQ ID NO:3) described in Example 9, except for the presence of nine additional bp situated 5' to the nucleotide at position number 1 of SEQ ID NO:3. These nine nucleotides encode the N-terminal tripeptide FRR which comprise amino acids 1-3 of SEQ ID NO:2, referred to herein as MRA-2. These three nucleotide codons are identical to the three codons found in the coding sequences upstream of the cleavage site between mesothelin and its precursor (Chang et al., 1996) and between MPF and its precursor (Kojima et al., 1995). Accordingly, the deduced soluble mesothelin related (SMR) antigen polypeptide sequence (SEQ ID NO: 13) is shown in FIG. 7A-B, as is a nucleic acid sequence (SEQ ID NO:14) encoding such SMR polypeptide (SEQ ID NO: 13). SMR (SEQ ID NO: 13) comprises the FRR N-terminal tripeptide identified in MRA-2 (SEQ ID NO: 2) plus the entire polypeptide sequence (SEQ ID NO: 1) of MRA-1 (SEQ ID NO: 1) as described above, the C-terminus of which is encoded by a nucleotide sequence that extends into a polyadenylation site but lacks a stop codon.

Example 11

Expression of MRA in an Ovarian Carcinoma Cell Line

In this example, detection of MRA-encoding nucleic acid sequences in a cDNA library derived from a human ovarian carcinoma cell line is described. RNA is extracted from cultured 3997 ovarian carcinoma cells (generated as described above, see. e.g., Hellstrom et al., 1990 *Cancer Res.* 50:2183) and used to produce a cDNA library by reverse transcription using the Marathon™ cDNA amplification kit (Clontech, Palo Alto, Calif.) according to the manufacturer's instructions. The library is cloned in pCDNA3-Zeo (InVitrogen, Inc., San Diego, Calif.) and screened by oligonucleotide probe hybridization to northern blots. The following oligonucleotide is synthesized corresponding to a region of the MRA 82 nucleotide insert described in Example 9:

i35: 5'-CCA GGG CTG GGG GCA GAG CTG GGG GGG CGT GGA GGT G-3' SEQ ID NO:12

End-labeling of i35 with [$^{32}$P] is performed using the Primer Extension System (Promega, Madison, Wis.) according to the supplier's instructions, and the labeled oligonucleotide is used to probe a northern blot containing electrophoretically separated RNA samples from various human tissues (MTN™ Mutitple Tissue Northern Blot, Cat. No. 7760-1, Clontech, Palo Alto, Calif.), according to well known procedures. Individual clones identified by the screening assay are selected, amplified and sequenced as described in Example 10, to determine an MRA sequence from the ovarian carcinoma cell line.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of screening for the presence of a malignant condition in a subject comprising: contacting a biological sample from a subject with at least one antibody specific for a mesothelin related antigen polypeptide, the mesothelin related antigen polypeptide having an amino acid sequence selected from the group consisting of SEQ ID NO: 1, SEQ ID NO: 2 and SEQ ID NO: 13, to determine the presence in said biological sample of a molecule naturally occurring in soluble form in said sample and having an antigenic determinant that is reactive with said at least one antibody, under conditions and for a time sufficient to detect binding of said antibody to said antigenic determinant, and therefrom detecting the presence of a malignant condition.

2. The method of claim 1 wherein the biological sample is selected from the group consisting of blood, serum, serosal fluid, plasma, urine, ascites fluid, pleural fluid, pericardial fluid, peritoneal fluid, abdominal fluid, and lavage fluid.

3. The method of claim 1 wherein the biological sample is serum.

4. The method of claim 1 wherein the biological sample is plasma.

5. The method of claim 1 wherein the biological sample is ascites fluid.

6. The method of claim 1 wherein the antibody comprises a polyclonal antibody.

7. The method of claim 1 wherein the antibody comprises an affinity purified antibody.

8. The method of claim 1 wherein the antibody comprises a monoclonal antibody.

9. The method of claim 1 wherein the antibody comprises a recombinant antibody.

10. The method of claim 1 wherein the antibody comprises a chimeric antibody.

11. The method of claim 1 wherein the antibody comprises a humanized antibody.

12. The method of claim 1 wherein the antibody comprises a single chain antibody.

13. The method of claim 1 wherein detection of binding of the antibody to an antigenic determinant comprises detection of a radionuclide.

14. The method of claim 1 wherein detection of binding of the antibody to an antigenic determinant comprises detection of a fluorophore.

15. The method of claim 1 wherein detection of binding of the antibody to an antigenic determinant comprises detection of a binding event between an avidin molecule and a biotin molecule.

16. The method of claim 1 wherein detection of binding of the antibody to an antigenic determinant comprises detection of a binding event between a streptavidin molecule and a biotin molecule.

17. The method of claim 1 wherein detection of binding of the antibody to an antigenic determinant comprises spectrophotometric detection of a product of an enzyme reaction.

18. The method of claim 1 wherein said at least one antibody is detectably labeled.

19. The method of claim 1 wherein said at least one antibody is not detectably labeled and wherein detection of binding of the antibody to an antigenic determinant is indirect.

20. The method of claim 1 wherein the malignant condition is selected from the group consisting of adenocarcinoma, mesothelioma, ovarian carcinoma, pancreatic carcinoma and non-small cell lung carcinoma.

21. A method of screening for the presence of a malignant condition in a subject comprising: contacting a pleural fluid from a subject with at least one antibody specific for a mesothelin related antigen polypeptide, the mesothelin related antigen polypeptide having an amino acid sequence selected from the group consisting of SEQ ID NO: 1, SEQ ID NO: 2 and SEQ ID NO: 13, to determine the presence in said biological sample of a molecule naturally occurring in soluble form in said sample and having an antigenic determinant that is reactive with said at least one antibody, under conditions and for a time sufficient to detect binding of said antibody to said antigenic determinant, and therefrom detecting the presence of a malignant condition.

22. A method of screening for the presence of a malignant condition in a subject comprising: contacting a biological sample from a subject with at least one antibody specific for a human mesothelin related antigen polypeptide, the mesothelin related antigen polypeptide having an amino acid sequence selected from the group consisting of SEQ ID NO: 1, SEQ ID NO: 2 and SEQ ID NO: 13, to determine the presence in said biological sample of a molecule naturally occurring in soluble form in said sample and having an antigenic determinant that is reactive with said antibody, under conditions and for a time sufficient to detect binding of said at least one antibody to said antigenic determinant, wherein said at least one antibody immunospecifically binds to mesothelin related antigen, and therefrom detecting the presence of a malignant condition.

23. A method of screening for the presence of a malignant condition in a subject comprising: contacting a biological sample from a subject with at least one immobilized first antibody specific for a mesothelin related antigen polypeptide, the mesothelin related antigen polypeptide having an amino acid sequence selected from the group consisting of SEQ ID NO: 1, SEQ ID NO: 2 and SEQ ID NO: 13, to determine the presence in said biological sample of a molecule naturally occurring in soluble form in said sample, under conditions and for a time sufficient to specifically bind said at least one immobilized first antibody to said mesothelin related antigen polypeptide and thereby form an immune complex; removing constituents of the sample that do not specifically bind to said at least one immobilized first antibody; and contacting said immune complex with at least one second antibody specific for a mesothelin related antigen polypeptide, wherein the antigen combining site of said at least one second antibody does not competitively inhibit the antigen combining site of said at least one immobilized first antibody, under conditions and for a time sufficient to detect specific binding of said at least one second antibody to said mesothelin related antigen polypeptide, and therefrom detecting the presence of a malignant condition.

24. The method of any one of claims 1-5, 21, 6-20, 22, and 23, further comprising determining the presence in said sample of at least one soluble marker of a malignant condition selected from the group consisting of carcinoembryonic antigen, CA125, sialyl TN, squamous cell carcinoma antigen, tissue polypeptide antigen, and placental alkaline phosphatase.

25. A method of screening for the presence of a malignant condition in a subject comprising: contacting each of (i) a first biological sample from a first subject suspected of having a malignant condition, and (ii) a second biological sample from a second subject known to be free of a malignant condition, with at least one antibody specific for a mesothelin related antigen polypeptide, the mesothelin related antigen polypeptide having an amino acid sequence selected from the group consisting of SEQ ID NO: 1, SEQ ID NO: 2 and SEQ ID NO: 13, to determine the presence in each of said first and second biological samples of a molecule naturally occurring in soluble form in said samples and having an antigenic determinant that is reactive with said at least one antibody, under conditions and for a time sufficient to detect binding of said antibody to said antigenic determinant, and comparing a level of detectable binding of said antibody to said antigenic determinant in the first biological sample to a level of detectable binding of said antibody to said antigenic determinant in the second biological sample, and therefrom detecting the presence of a malignant condition.

26. A method of screening for the presence of a malignant condition in a subject comprising: detecting in a biological sample from the subject the presence of an antibody that immunospecifically binds to a mesothelin related antigen polypeptide, wherein the amino acid sequence of the mesothelin related antigen polypeptide consists of SEQ ID NO:1, SEQ ID NO:2 or SEQ ID NO:13.

27. A method of screening for the presence of a malignant condition in a subject comprising: contacting a biological sample from a subject with a detectably labeled mesothelin related antigen polypeptide, the mesothelin related antigen polypeptide having an amino acid sequence selected from the group consisting of SEQ ID NO: 1, SEQ ID NO: 2 and SEQ ID NO: 13, under conditions and for a time sufficient to detect binding to said mesothelin related antigen polypeptide of an antibody naturally occurring in soluble form in said sample, and therefrom detecting the presence of a malignant condition.

* * * * *

SEQUENCE LISTING

<160> NUMBER OF SEQ ID NOS: 18

<210> SEQ ID NO 1
<211> LENGTH: 399
<212> TYPE: PRT
<213> ORGANISM: Homo sapien

<400> SEQUENCE: 1

| Glu | Val | Glu | Lys | Thr | Ala | Cys | Pro | Ser | Gly | Lys | Lys | Ala | Arg | Glu | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Glu | Ser | Leu | Ile | Phe | Tyr | Lys | Lys | Trp | Glu | Leu | Glu | Ala | Cys | Val |
|     |     |     | 20  |     |     |     |     | 25  |     |     |     |     | 30  |     |     |

| Asp | Ala | Ala | Leu | Leu | Ala | Thr | Gln | Met | Asp | Arg | Val | Asn | Ala | Ile | Pro |
|     |     | 35  |     |     |     |     | 40  |     |     |     |     | 45  |     |     |     |

| Phe | Thr | Tyr | Glu | Gln | Leu | Asp | Val | Leu | Lys | His | Lys | Leu | Asp | Glu | Leu |
|     | 50  |     |     |     |     | 55  |     |     |     |     | 60  |     |     |     |     |

| Tyr | Pro | Gln | Gly | Tyr | Pro | Glu | Ser | Val | Ile | Gln | His | Leu | Gly | Tyr | Leu |
| 65  |     |     |     |     | 70  |     |     |     |     | 75  |     |     |     |     | 80  |

| Phe | Leu | Lys | Met | Ser | Pro | Glu | Asp | Ile | Arg | Lys | Trp | Asn | Val | Thr | Ser |
|     |     |     |     | 85  |     |     |     |     | 90  |     |     |     |     | 95  |     |

| Leu | Glu | Thr | Leu | Lys | Ala | Leu | Leu | Glu | Val | Asn | Lys | Gly | His | Glu | Met |
|     |     |     | 100 |     |     |     |     | 105 |     |     |     |     | 110 |     |     |

| Ser | Pro | Gln | Val | Ala | Thr | Leu | Ile | Asp | Arg | Phe | Val | Lys | Gly | Arg | Gly |
|     |     | 115 |     |     |     |     | 120 |     |     |     |     | 125 |     |     |     |

| Gln | Leu | Asp | Lys | Asp | Thr | Leu | Asp | Thr | Leu | Thr | Ala | Phe | Tyr | Pro | Gly |
|     | 130 |     |     |     |     | 135 |     |     |     |     | 140 |     |     |     |     |

| Tyr | Leu | Cys | Ser | Leu | Ser | Pro | Glu | Glu | Leu | Ser | Ser | Val | Pro | Pro | Ser |
| 145 |     |     |     |     | 150 |     |     |     |     | 155 |     |     |     |     | 160 |

| Ser | Ile | Trp | Ala | Val | Arg | Pro | Gln | Asp | Leu | Asp | Thr | Cys | Asp | Pro | Arg |
|     |     |     |     | 165 |     |     |     |     | 170 |     |     |     |     | 175 |     |

| Gln | Leu | Asp | Val | Leu | Tyr | Pro | Lys | Ala | Arg | Leu | Ala | Phe | Gln | Asn | Met |
|     |     |     | 180 |     |     |     |     | 185 |     |     |     |     | 190 |     |     |

| Asn | Gly | Ser | Glu | Tyr | Phe | Val | Lys | Ile | Gln | Ser | Phe | Leu | Gly | Gly | Ala |
|     |     | 195 |     |     |     |     | 200 |     |     |     |     | 205 |     |     |     |

| Pro | Thr | Glu | Asp | Leu | Lys | Ala | Leu | Ser | Gln | Gln | Asn | Val | Ser | Met | Asp |
|     | 210 |     |     |     |     | 215 |     |     |     |     | 220 |     |     |     |     |

| Leu | Ala | Thr | Phe | Met | Lys | Leu | Arg | Thr | Asp | Ala | Val | Leu | Pro | Leu | Thr |
| 225 |     |     |     |     | 230 |     |     |     |     | 235 |     |     |     |     | 240 |

| Val | Ala | Glu | Val | Gln | Lys | Leu | Leu | Gly | Pro | His | Val | Glu | Gly | Leu | Lys |
|     |     |     |     | 245 |     |     |     |     | 250 |     |     |     |     | 255 |     |

| Ala | Glu | Glu | Arg | His | Arg | Pro | Val | Arg | Asp | Trp | Ile | Leu | Arg | Gln | Arg |
|     |     |     | 260 |     |     |     |     | 265 |     |     |     |     | 270 |     |     |

| Gln | Asp | Asp | Leu | Asp | Thr | Leu | Gly | Leu | Gly | Leu | Gln | Gly | Gly | Ile | Pro |
|     |     | 275 |     |     |     |     | 280 |     |     |     |     | 285 |     |     |     |

| Asn | Gly | Tyr | Leu | Val | Leu | Asp | Leu | Ser | Val | Gln | Gly | Arg | Gly | Gly |
|     | 290 |     |     |     |     | 295 |     |     |     |     | 300 |     |     |     |

| Gln | Ala | Arg | Ala | Gly | Arg | Ala | Gly | Gly | Val | Gly | Ala | Leu |
| 305 |     |     |     | 310 |     |     |     |     | 315 |     |     | 320 |

| Ser | His | Pro | Ser | Leu | Cys | Arg | Gly | Pro | Leu | Gly | Asp | Ala | Leu | Pro | Pro |
|     |     |     |     | 325 |     |     |     |     | 330 |     |     |     |     | 335 |     |

| Arg | Thr | Trp | Thr | Cys | Ser | His | Arg | Pro | Gly | Thr | Ala | Pro | Ser | Leu | His |
|     |     |     |     | 340 |     |     |     |     | 345 |     |     |     |     | 350 |     |

| Pro | Gly | Leu | Arg | Ala | Pro | Leu | Pro | Cys | Trp | Pro | Gln | Pro | Cys | Trp | Gly |

```
                355                 360                 365
Ser Pro Pro Gly Gln Glu Gln Ala Arg Val Ile Pro Val Pro Gln
            370                 375                 380
Glu Asn Ser Arg Ser Val Asn Gly Asn Met Pro Pro Ala Asp Thr
385                 390                 395

<210> SEQ ID NO 2
<211> LENGTH: 328
<212> TYPE: PRT
<213> ORGANISM: Homo sapien

<400> SEQUENCE: 2

Phe Arg Arg Glu Val Glu Lys Thr Ala Cys Pro Ser Gly Lys Lys Ala
1               5                   10                  15
Arg Glu Ile Asp Glu Ser Leu Ile Phe Tyr Lys Lys Trp Glu Leu Glu
            20                  25                  30
Ala Cys Val Asp Ala Ala Leu Leu Ala Thr Gln Met Asp Arg Val Asn
        35                  40                  45
Ala Ile Pro Phe Thr Tyr Glu Gln Leu Asp Val Leu Lys His Lys Leu
    50                  55                  60
Asp Glu Leu Tyr Pro Gln Gly Tyr Pro Glu Ser Val Ile Gln His Leu
65                  70                  75                  80
Gly Tyr Leu Phe Leu Lys Met Ser Pro Glu Asp Ile Arg Lys Trp Asn
                85                  90                  95
Val Thr Ser Leu Glu Thr Leu Lys Ala Leu Leu Glu Val Asn Lys Gly
            100                 105                 110
His Glu Met Ser Pro Gln Val Ala Thr Leu Ile Asp Arg Phe Val Lys
        115                 120                 125
Gly Arg Gly Gln Leu Asp Lys Asp Thr Leu Asp Thr Leu Thr Ala Phe
    130                 135                 140
Tyr Pro Gly Tyr Leu Cys Ser Leu Ser Pro Glu Glu Leu Ser Ser Val
145                 150                 155                 160
Pro Pro Ser Ser Ile Trp Ala Val Arg Pro Gln Asp Leu Asp Thr Cys
                165                 170                 175
Asp Pro Arg Gln Leu Asp Val Leu Tyr Pro Lys Ala Arg Leu Ala Phe
            180                 185                 190
Gln Asn Met Asn Gly Ser Glu Tyr Phe Val Lys Ile Gln Ser Phe Leu
        195                 200                 205
Gly Gly Ala Pro Thr Glu Asp Leu Lys Ala Leu Ser Gln Gln Asn Val
    210                 215                 220
Ser Met Asp Leu Ala Thr Phe Met Lys Leu Arg Thr Asp Ala Val Leu
225                 230                 235                 240
Pro Leu Thr Val Ala Glu Val Gln Lys Leu Leu Gly Pro His Val Glu
                245                 250                 255
Gly Leu Lys Ala Glu Glu Arg His Arg Pro Val Arg Asp Trp Ile Leu
            260                 265                 270
Arg Gln Arg Gln Asp Asp Leu Asp Thr Leu Gly Leu Gly Leu Gln Gly
        275                 280                 285
Gly Ile Pro Asn Gly Tyr Leu Val Leu Asp Leu Ser Val Gln Gly Gly
    290                 295                 300
Arg Gly Gly Gln Ala Arg Ala Gly Gly Arg Ala Gly Gly Val Glu Val
305                 310                 315                 320
Gly Ala Leu Ser His Pro Ser Leu
                325
```

<210> SEQ ID NO 3
<211> LENGTH: 1198
<212> TYPE: DNA
<213> ORGANISM: Homo sapien

<400> SEQUENCE: 3

```
gaagtggaga agacagcctg tccttcaggc aagaaggccc gcgagataga cgagagcctc      60
atcttctaca agaagtggga gctggaagcc tgcgtggatg cggccctgct ggccacccag     120
atggaccgcg tgaacgccat ccccttcacc tacgagcagc tggacgtcct aaagcataaa     180
ctggatgagc tctacccaca aggttacccc gagtctgtga ccagcacct gggctacctc      240
ttcctcaaga tgagccctga ggacattcgc aagtggaatg tgacgtccct ggagaccctg     300
aaggctttgc ttgaagtcaa caagggcac gaaatgagtc tcaggtggc caccctgatc       360
gaccgctttg tgaagggaag gggccagcta gacaaagaca ccctagacac cctgaccgcc     420
ttctaccctg gtacctgtg ctccctcagc ccgaggagc tgagctccgt gccccccagc       480
agcatctggg cggtcaggcc caggacctg gacacgtgtg acccaaggca gctggacgtc      540
ctctatccca aggcccgcct tgcttccag aacatgaacg gtccgaata cttcgtgaag       600
atccagtcct tcctgggtgg ggccccacg gaggatttga aggcgctcag tcagcagaat      660
gtgagcatgg acttggccac gttcatgaag ctgcggacgg atgcggtgct gccgttgact     720
gtggctgagg tgcagaaact tctgggaccc cacgtggagg gcctgaaggc ggaggagcgg     780
caccgcccgg tgcgggactg gatcctacgg cagcggcagg acgacctgga cacgctgggg     840
ctggggctac agggcggcat ccccaacggc tacctggtcc tagacctcag cgtgcaaggt    900
gggcggggcg ccaggccag ggctgggggc agagctgggg gcgtggaggt gggcgctctg      960
agtcacccct ctctctgtag aggccctctc ggggacgccc tgcctcctag gacctggacc    1020
tgttctcacc gtcctggcac tgctcctagc ctccaccctg gctgagggc cccactccct     1080
tgctggcccc agccctgctg gggatccccg cctggccagg agcaggcacg ggtgatcccc    1140
gttccacccc aagagaactc gcgctcagta acgggaaca tgcccctgc agacacgt       1198
```

<210> SEQ ID NO 4
<211> LENGTH: 985
<212> TYPE: DNA
<213> ORGANISM: Homo sapien

<400> SEQUENCE: 4

```
ttccggcggg aagtggagaa gacagcctgt ccttcaggca agaaggcccg cgagatagac      60
gagagcctca tcttctacaa gaagtgggag ctggaagcct gcgtggatgc ggccctgctg     120
gccacccaga tggaccgcgt gaacgccatc cccttcacct acgagcagct ggacgtccta     180
aagcataaac tggatgagct ctacccacaa ggttaccccg agtctgtgat ccagcacctg     240
gctacctct tcctcaagat gagccctgag acattcgca agtggaatgt gacgtccctg       300
gagaccctga aggctttgct tgaagtcaac aagggcacg aaatgagtcc tcaggtggcc      360
accctgatcg accgctttgt gaagggaagg ggccagctag acaaagacac cctagacacc     420
ctgaccgcct tctaccctgg gtacctgtgc tccctcagcc cgaggagct gagctccgtg      480
ccccccagca gcatctgggc ggtcaggccc aggacctgg acacgtgtga cccaaggcag     540
ctggacgtcc tctatcccaa ggcccgcctt gctttccaga acatgaacgg tccgaatac     600
ttcgtgaaga tccagtcctt cctgggtggg gccccacgg aggatttgaa ggcgctcagt     660
cagcagaatg tgagcatgga cttggccacg ttcatgaagc tgcggacgga tgcggtgctg    720
```

-continued

```
ccgttgactg tggctgaggt gcagaaactt ctgggacccc acgtggaggg cctgaaggcg      780
gaggagcggc accgcccggt gcgggactgg atcctacggc agcggcagga cgacctggac      840
acgctggggc tggggctaca gggcggcatc cccaacggct acctggtcct agacctcagc      900
gtgcaaggtg gcgggggcgg ccaggccagg gctgggggca gagctggggg cgtggaggtg      960
ggcgctctga gtcacccctc tctct                                            985
```

<210> SEQ ID NO 5
<211> LENGTH: 19
<212> TYPE: PRT
<213> ORGANISM: Homo sapien

<400> SEQUENCE: 5

Glu Val Glu Lys Thr Ala Cys Pro Ser Gly Lys Lys Ala Arg Glu Ile
 1               5                   10                  15

Asp Glu Ser

<210> SEQ ID NO 6
<211> LENGTH: 27
<212> TYPE: DNA
<213> ORGANISM: Artificial Sequence
<220> FEATURE:
<223> OTHER INFORMATION: PCR primer

<400> SEQUENCE: 6
ggaagtggag aagacagcct gtccttc                                          27

<210> SEQ ID NO 7
<211> LENGTH: 25
<212> TYPE: DNA
<213> ORGANISM: Artificial Sequence
<220> FEATURE:
<223> OTHER INFORMATION: PCR primer

<400> SEQUENCE: 7
gcgctctgag tcacccctct ctctg                                            25

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
agaaacttct gggacccac                                                   20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
gggacgtcac attccacttg                                                  20

<210> SEQ ID NO 10
<211> LENGTH: 28
<212> TYPE: DNA
<213> ORGANISM: Artificial Sequence
<220> FEATURE:
<223> OTHER INFORMATION: PCR primer

```
<400> SEQUENCE: 10
gaaggacagg ctgtcttctc cacttccc                                              28

<210> SEQ ID NO 11
<211> LENGTH: 23
<212> TYPE: DNA
<213> ORGANISM: Artificial Sequence
<220> FEATURE:
<223> OTHER INFORMATION: PCR primer

<400> SEQUENCE: 11
cagagagagg ggtgactcag agc                                                   23

<210> SEQ ID NO 12
<211> LENGTH: 37
<212> TYPE: DNA
<213> ORGANISM: Artificial Sequence
<220> FEATURE:
<223> OTHER INFORMATION: Oligonucleotide probe synthesized for
      hybrization in northern blots.

<400> SEQUENCE: 12
ccagggctgg gggcagagct ggggggcgt ggaggtg                                     37

<210> SEQ ID NO 13
<211> LENGTH: 402
<212> TYPE: PRT
<213> ORGANISM: Homo sapien

<400> SEQUENCE: 13
```

Phe Arg Arg Glu Val Glu Lys Thr Ala Cys Pro Ser Gly Lys Lys Ala
 1               5                  10                  15

Arg Glu Ile Asp Glu Ser Leu Ile Phe Tyr Lys Lys Trp Glu Leu Glu
             20                  25                  30

Ala Cys Val Asp Ala Ala Leu Leu Ala Thr Gln Met Asp Arg Val Asn
         35                  40                  45

Ala Ile Pro Phe Thr Tyr Glu Gln Leu Asp Val Leu Lys His Lys Leu
     50                  55                  60

Asp Glu Leu Tyr Pro Gln Gly Tyr Pro Glu Ser Val Ile Gln His Leu
 65                  70                  75                  80

Gly Tyr Leu Phe Leu Lys Met Ser Pro Glu Asp Ile Arg Lys Trp Asn
                 85                  90                  95

Val Thr Ser Leu Glu Thr Leu Lys Ala Leu Leu Glu Val Asn Lys Gly
            100                 105                 110

His Glu Met Ser Pro Gln Val Ala Thr Leu Ile Asp Arg Phe Val Lys
        115                 120                 125

Gly Arg Gly Gln Leu Asp Lys Asp Thr Leu Asp Thr Leu Thr Ala Phe
    130                 135                 140

Tyr Pro Gly Tyr Leu Cys Ser Leu Ser Pro Glu Leu Ser Ser Val
145                 150                 155                 160

Pro Pro Ser Ser Ile Trp Ala Val Arg Pro Gln Asp Leu Asp Thr Cys
                165                 170                 175

Asp Pro Arg Gln Leu Asp Val Leu Tyr Pro Lys Ala Arg Leu Ala Phe
            180                 185                 190

Gln Asn Met Asn Gly Ser Glu Tyr Phe Val Lys Ile Gln Ser Phe Leu
        195                 200                 205

Gly Gly Ala Pro Thr Glu Asp Leu Lys Ala Leu Ser Gln Gln Asn Val
    210                 215                 220

Ser Met Asp Leu Ala Thr Phe Met Lys Leu Arg Thr Asp Ala Val Leu
225                 230                 235                 240

Pro Leu Thr Val Ala Glu Val Gln Lys Leu Leu Gly Pro His Val Glu
            245                 250                 255

Gly Leu Lys Ala Glu Glu Arg His Arg Pro Val Arg Asp Trp Ile Leu
        260                 265                 270

Arg Gln Arg Gln Asp Asp Leu Asp Thr Leu Gly Leu Gly Leu Gln Gly
    275                 280                 285

Gly Ile Pro Asn Gly Tyr Leu Val Leu Asp Leu Ser Val Gln Gly Gly
290                 295                 300

Arg Gly Gly Gln Ala Arg Ala Gly Gly Arg Ala Gly Gly Val Glu Val
305                 310                 315                 320

Gly Ala Leu Ser His Pro Ser Leu Cys Arg Gly Pro Leu Gly Asp Ala
            325                 330                 335

Leu Pro Pro Arg Thr Trp Thr Cys Ser His Arg Pro Gly Thr Ala Pro
        340                 345                 350

Ser Leu His Pro Gly Leu Arg Ala Pro Leu Pro Cys Trp Pro Gln Pro
    355                 360                 365

Cys Trp Gly Ser Pro Pro Gly Gln Glu Gln Ala Arg Val Ile Pro Val
370                 375                 380

Pro Pro Gln Glu Asn Ser Arg Ser Val Asn Gly Asn Met Pro Pro Ala
385                 390                 395                 400

Asp Thr

<210> SEQ ID NO 14
<211> LENGTH: 1207
<212> TYPE: DNA
<213> ORGANISM: Homo sapien

<400> SEQUENCE: 14
ttccggcggg aagtggagaa gacagcctgt ccttcaggca agaaggcccg cgagatagac      60
gagagcctca tcttctacaa gaagtgggag ctggaagcct gcgtggatgc ggccctgctg     120
gccacccaga tggaccgcgt gaacgccatc cccttcacct acgagcagct ggacgtccta     180
aagcataaac tggatgagct ctacccacaa ggttacccccg agtctgtgat ccagcacctg     240
ggctacctct tcctcaagat gagccctgag gacattcgca agtggaatgt gacgtccctg     300
gagaccctga aggctttgct tgaagtcaac aaagggcacg aaatgagtcc tcaggtggcc     360
accctgatcg accgctttgt gaagggaagg ggccagctag acaaagacac cctagacacc     420
ctgaccgcct ctacccctgg gtacctgtgc tccctcagcc ccgaggagct gagctccgtg     480 cccccccagca gcatctgggc ggtcaggccc caggacctgg acacgtgtga cccaaggcag     540
ctggacgtcc tctatcccaa ggcccgcctt gctttccaga acatgaacgg gtccgaatac     600
ttcgtgaaga tccagtcctt cctgggtggg gcccccacgg aggatttgaa ggcgctcagt     660
cagcagaatg tgagcatgga cttggccacg ttcatgaagc tgcggacgga tgcggtgctg     720
ccgttgactg tggctgaggt gcagaaactt ctgggacccc acgtggaggg cctgaaggcg     780
gaggagcggc accgcccggt gcgggactgg atcctacggc agcggcagga cgacctggac     840
acgctggggc tggggctaca gggcggcatc cccaacggct acctggtcct agacctcagc     900
gtgcaaggtg gcggggcgg ccaggccagg gctgggggca gagctggggg cgtggaggtg     960
ggcgctctga gtcacccctc tctctgtaga ggccctctcg ggacgccct gcctcctagg    1020 acctggacct gttctcaccg tcctggcact gctcctagcc tccaccctgg cctgagggcc    1080

```
ccactccctt gctggcccca gccctgctgg ggatccccgc ctggccagga gcaggcacgg    1140
gtgatccccg ttccacccca agagaactcg cgctcagtaa acgggaacat gccccctgca    1200
gacacgt                                                              1207
```

<210> SEQ ID NO 15
<211> LENGTH: 412
<212> TYPE: DNA
<213> ORGANISM: Homo sapien

<400> SEQUENCE: 15

```
acgtgtctgc agggggcatg ttcccgttta ctgagcgcga gttctcttgg ggtggaacgg     60
ggaccacccg tgcctgctcc tggccaggcg gggatcccca gcagggctgg ggccagcaag    120
ggagtggggc cctcaggcac gggtggaggc taggagcagt gccaggacgg tgagaacagg    180
tccaggtcct aggaggcagg gcgtccccga gaggacctct acagagagag gggtgactca    240
gagcgcccac ctccacgccc ccagctctgc ccccagccct ggcctggccg ccccgcccac    300
cttgcatgct gaggtctagg accaggtagc cgttggggat gccgccctgt agccccagcc    360
ccagcgtgtc caggtcgtcc tgccgctgcc gtgagatcca gtcccgcacc gg            412
```

<210> SEQ ID NO 16
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 16

```
tacgtgtctg caggggggcat gttcccgttt actgagcgcg agttctcttg gggtggaacg     60
gggaccaccc gtgcctgctc ctggccaggc ggggatcccc agcagggctg gtnccagcaa    120
gggagtgggg ccctcaggca gtggtggagg ctaggagcag tgccaggacg gtgagaacag    180
gtccaggtcc taggaggcag ggcgtccccg agaggtcctc tacagagaga ggggtgactc    240
agagcgccca cctccacgcc cccagctctg ccccagccc tggcctggcc gccccgccca    300
ccttgcatgc tgaggtctag gaccaggtag ccgttgggga tgccgccctg tagccccagc    360
cccagcgtgt ccaggtcgtc ctgccgctgc cgtagg                              396
```

<210> SEQ ID NO 17
<211> LENGTH: 427
<212> TYPE: DNA
<213> ORGANISM: Homo sapien

<400> SEQUENCE: 17

```
cacgtggagg gcctgaagcg gaggagcggc accgccggtc gggatctgga tcctacggca     60
gcggcaggac gacctggaca cgctggggct ggggctacag ggcggcatcc ccaacggcta    120
cctggtccta gacctcagca tgcaaggtgg gcggggcggc caggccaggg ctgggggcag    180 agctggggggc gtggaggtgg gcgctctgag tcacccctct ctctgtagag gccctctcgg    240
ggacgccctg cctcctagga cctgacctg ttctcaccgt cctggcactg ctcctagcct    300
ccaccctggc ctgagggccc actcccttgc tggccccagc cctgctggga atcccgcct    360 ggccaggagc aggcacgggt ggtccccgtt ccaccccaag agaactcgcg ctcagtaaac    420
gggaaca                                                              427
```

```
<210> SEQ ID NO 18
<211> LENGTH: 507
<212> TYPE: DNA
<213> ORGANISM: Homo sapien

<400> SEQUENCE: 18
tttttgagat ggagtcttgc tgtgtcacca ggctggagtg caatggaacg accttggctc        60
actgtaacct ccgcctccct ggttcaggag aatcacctga gcccaagagg tagaagctgc       120
agtgacccat gatggtgcca ctgtactccg cccaggcaac agagtgaggc cctgtctcaa       180
aaaaaaaaaa atgttttatc tgaacttgac aatctaataa taaaaattag tgacaatcag       240
tttactgaaa tgtgactttt ttttttttcc tcctctataa tttaggcctt ggaaaaccat       300
tgcagagtga atggaggcta ttcaggccta agggatgttt accttcttca tgagagttat       360
gatgatgtgc agcagagttt cttcctggca gagaccttga aatatttgga acctataatt       420
tccgacgacg aatcttcttc cacggggggca tgggttcctc cataggggggg gacaatttct     480 ccccaaactc ccccaaagga aaaaagg                                          507
```